(12) United States Patent
Olson

(10) Patent No.: US 7,718,844 B2
(45) Date of Patent: May 18, 2010

(54) ABSORBENT ARTICLE HAVING AN INTERIOR GRAPHIC

(75) Inventor: Christopher P. Olson, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 318 days.

(21) Appl. No.: 10/881,255

(22) Filed: Jun. 30, 2004

(65) Prior Publication Data

US 2006/0004333 A1 Jan. 5, 2006

(51) Int. Cl.
*A61F 13/15* (2006.01)
*A61F 13/20* (2006.01)

(52) U.S. Cl. .................................................. 604/361
(58) Field of Classification Search ................ 604/361
See application file for complete search history.

(56) References Cited

U.S. PATENT DOCUMENTS

| | | | |
|---|---|---|---|
| 2,249,867 A | 7/1941 | Snelling |
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,613,679 A | 10/1971 | Bijou |
| 3,675,654 A | 7/1972 | Baker et al. |
| 3,692,618 A | 9/1972 | Dorschnet et al. |
| 3,702,610 A | 11/1972 | Sheppard et al. |
| 3,802,817 A | 4/1974 | Matsuki et al. |
| 4,022,211 A | 5/1977 | Timmons et al. |
| 4,100,324 A | 7/1978 | Anderson et al. |
| 4,284,703 A | 8/1981 | Inoue et al. |
| 4,430,563 A | 2/1984 | Harrington |
| 4,444,193 A | 4/1984 | Fogt et al. |
| 4,663,220 A | 5/1987 | Wisneski et al. |
| 4,673,403 A | 6/1987 | Lassen et al. |
| 4,704,116 A | 11/1987 | Enloe |

(Continued)

FOREIGN PATENT DOCUMENTS

EP     203715  A2    4/1985

(Continued)

OTHER PUBLICATIONS

International Search Report for PCT/US2005/022820 dated Jan. 4, 2006, 3 pages.

(Continued)

*Primary Examiner*—Melanie J Hand
(74) *Attorney, Agent, or Firm*—Armstrong Teasdale, LLP

(57) ABSTRACT

An absorbent article has an outer cover at least in part defining the outer surface of the article and a liner in opposed relationship with the outer cover and at least in part defining the inner surface of the article. An absorbent structure is disposed between the liner and the outer cover. At least one graphic is visible from the inner surface of the article. The at least one graphic disposed intermediate the inner surface and the outer surface of the article and being free from direct contact with the liner. The article being configured such that the graphic is visible from the inner surface of the article. A process for manufacturing an absorbent article having a graphic visible from the inner surface of the article is provided.

19 Claims, 13 Drawing Sheets

U.S. PATENT DOCUMENTS

| | | |
|---|---|---|
| 4,896,600 A | 1/1990 | Rogge et al. |
| 4,924,084 A | 5/1990 | Lask et al. |
| 4,931,051 A | 6/1990 | Castello |
| 4,940,464 A | 7/1990 | Van Gompel et al. |
| 5,046,272 A | 9/1991 | Vogt et al. |
| 5,104,116 A | 4/1992 | Pohjola |
| 5,114,781 A | 5/1992 | Morman |
| 5,116,662 A | 5/1992 | Morman |
| 5,213,881 A | 5/1993 | Timmons et al. |
| 5,224,405 A | 7/1993 | Pohjola |
| 5,226,992 A | 7/1993 | Morman |
| 5,284,703 A | 2/1994 | Everhart et al. |
| 5,341,127 A | 8/1994 | Smith |
| 5,350,624 A | 9/1994 | Georger et al. |
| H1376 H | 11/1994 | Osborn, III et al. |
| 5,458,590 A | 10/1995 | Schleinz et al. |
| 5,458,592 A | 10/1995 | Abuto et al. |
| 5,468,236 A | 11/1995 | Everhart et al. |
| 5,486,166 A | 1/1996 | Bishop et al. |
| 5,490,846 A | 2/1996 | Ellis et al. |
| 5,566,616 A | 10/1996 | Schleinz et al. |
| 5,568,128 A | 10/1996 | Nair |
| 5,645,542 A | 7/1997 | Anjur et al. |
| 5,647,863 A | 7/1997 | Hammons et al. |
| 5,649,914 A | 7/1997 | Glaug et al. |
| 5,683,752 A | 11/1997 | Popp et al. |
| 5,702,376 A | 12/1997 | Glaug et al. |
| 5,704,116 A | 1/1998 | Gamota et al. |
| 5,766,389 A | 6/1998 | Brandon et al. |
| 5,797,892 A | 8/1998 | Glaug et al. |
| 5,820,973 A | 10/1998 | Dodge, II et al. |
| 5,883,028 A | 3/1999 | Morman et al. |
| 5,897,541 A | 4/1999 | Uitenbroek et al. |
| 5,902,296 A | 5/1999 | Fluyeras |
| 5,964,743 A | 10/1999 | Abuto et al. |
| 6,231,557 B1 | 5/2001 | Krautkramer et al. |
| 6,284,942 B1 | 9/2001 | Rabin |
| 6,297,424 B1 * | 10/2001 | Olson et al. ............ 604/361 |
| 6,307,119 B1 | 10/2001 | Cammarota et al. |
| 6,362,389 B1 | 3/2002 | McDowall et al. |
| 6,384,728 B1 | 5/2002 | Kanor et al. |
| 6,464,635 B1 | 10/2002 | Cerrato et al. |
| 6,515,194 B2 | 2/2003 | Neading et al. |
| 6,576,810 B1 | 6/2003 | Underhill et al. |
| 6,583,722 B2 | 6/2003 | Jeutter et al. |
| 6,596,918 B1 | 7/2003 | Wehrle et al. |
| 6,627,786 B2 | 9/2003 | Roe et al. |
| 6,642,427 B2 | 11/2003 | Roe et al. |
| 6,645,190 B1 | 11/2003 | Olson et al. |
| 6,652,686 B1 | 11/2003 | Coenen et al. |
| 6,710,221 B1 | 3/2004 | Pierce et al. |
| 6,723,034 B2 | 4/2004 | Durrance et al. |
| 6,726,668 B2 | 4/2004 | Underhill et al. |
| 2001/0031954 A1 | 10/2001 | Jordan et al. |
| 2001/0049513 A1 | 12/2001 | Neading et al. |
| 2001/0053898 A1 | 12/2001 | Olson et al. |
| 2002/0007162 A1 | 1/2002 | Cammarota et al. |
| 2003/0014025 A1 | 1/2003 | Allen et al. |
| 2003/0019374 A1 | 1/2003 | Harte |
| 2003/0045845 A1 | 3/2003 | Yoshioka |
| 2003/0073966 A1 | 4/2003 | Sosalla et al. |
| 2003/0105443 A1 | 6/2003 | Ohnishi et al. |
| 2003/0114807 A1 | 6/2003 | Underhill et al. |
| 2003/0114821 A1 | 6/2003 | Underhill et al. |
| 2003/0125682 A1 | 7/2003 | Olson et al. |
| 2003/0158530 A1 | 8/2003 | Diehl et al. |
| 2003/0199845 A1 | 10/2003 | Roe et al. |
| 2004/0015145 A1 | 1/2004 | Miura et al. |
| 2004/0064113 A1 | 4/2004 | Erdman |
| 2004/0143231 A1 | 7/2004 | Nair et al. |
| 2005/0065489 A1 | 3/2005 | Driskell et al. |
| 2005/0096612 A1 * | 5/2005 | Davis et al. ............ 604/361 |

FOREIGN PATENT DOCUMENTS

| | | |
|---|---|---|
| EP | 217032 | 4/1987 |
| EP | 0 876 809 A1 | 11/1998 |
| EP | 1216673 | 6/2002 |
| EP | 1216674 | 6/2002 |
| EP | 1 295 711 A1 | 3/2003 |
| JP | 2004236826 | 8/2004 |
| WO | WO 94/12133 A1 | 6/1994 |
| WO | WO 96/31175 A1 | 10/1996 |
| WO | WO 99/02985 | 7/1997 |
| WO | WO 00/76558 | 6/1999 |
| WO | WO 00/37009 A2 | 6/2000 |
| WO | WO 01/41691 A1 | 6/2001 |
| WO | WO 02/091968 A2 | 11/2002 |
| WO | WO 01/88245 A2 | 6/2003 |
| WO | WO 03/051254 A2 | 6/2003 |
| WO | 03070137 D1 | 8/2003 |
| WO | WO 03/070137 A1 | 8/2003 |
| WO | WO 2005/041834 A1 | 5/2005 |

OTHER PUBLICATIONS

International Search Report for PCT/US2005/014901 dated Aug. 17, 2005, 3 pages.
Training Pants Having Internal Non-Active Graphics.
Absorbent Undergarment Having Internal Non-Active Graphics (Admitted prior art).

* cited by examiner

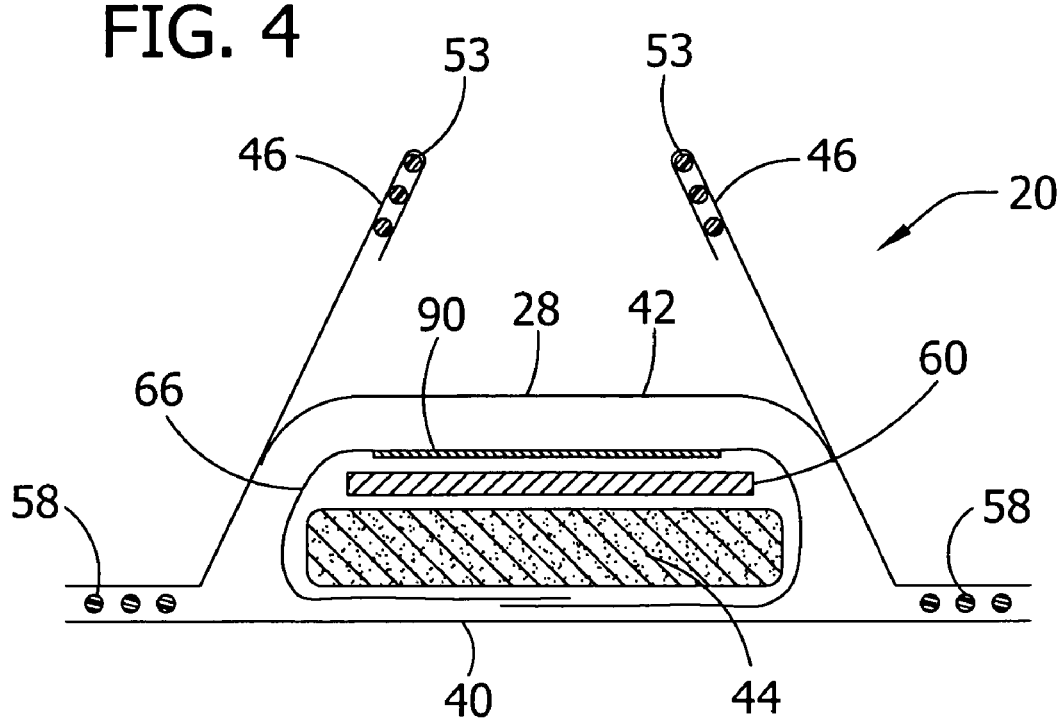
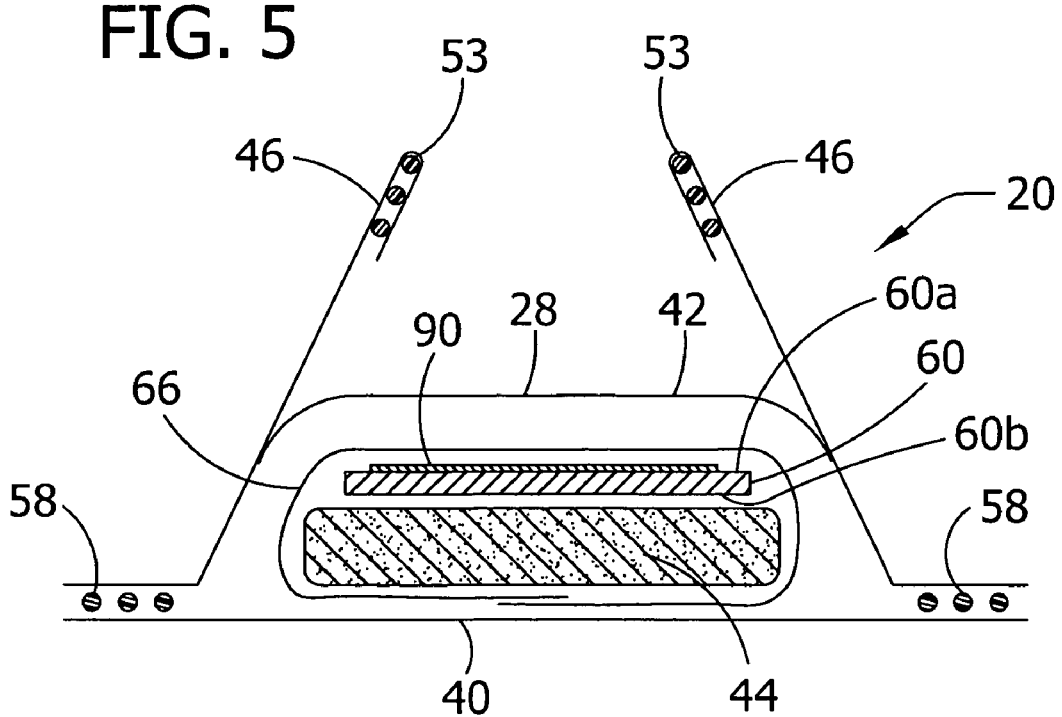

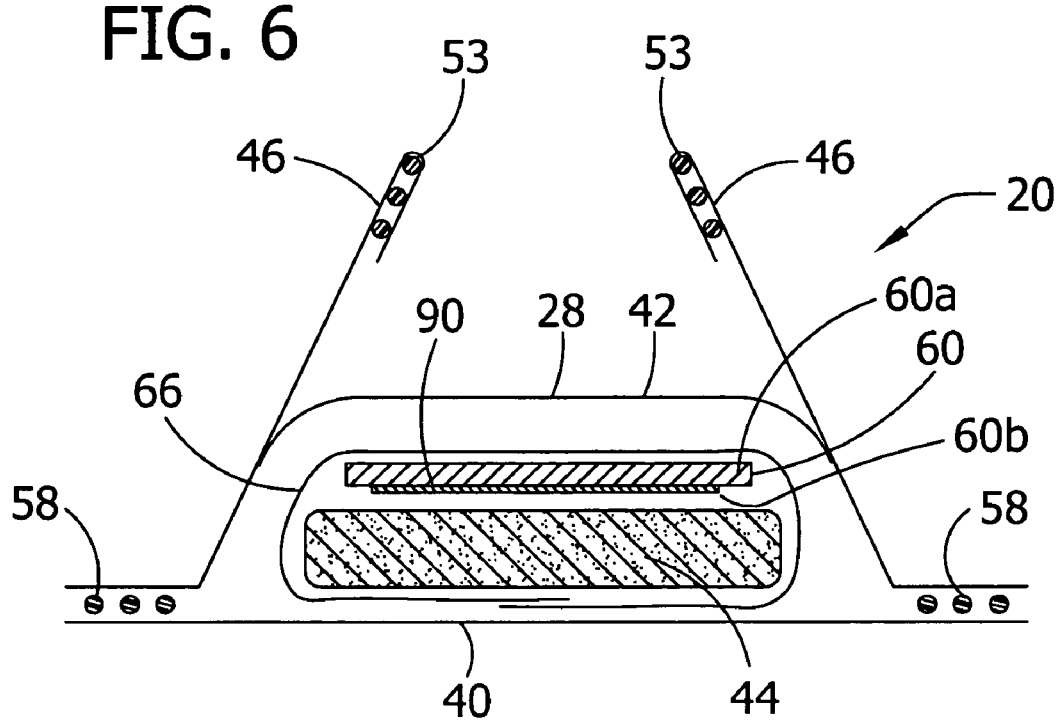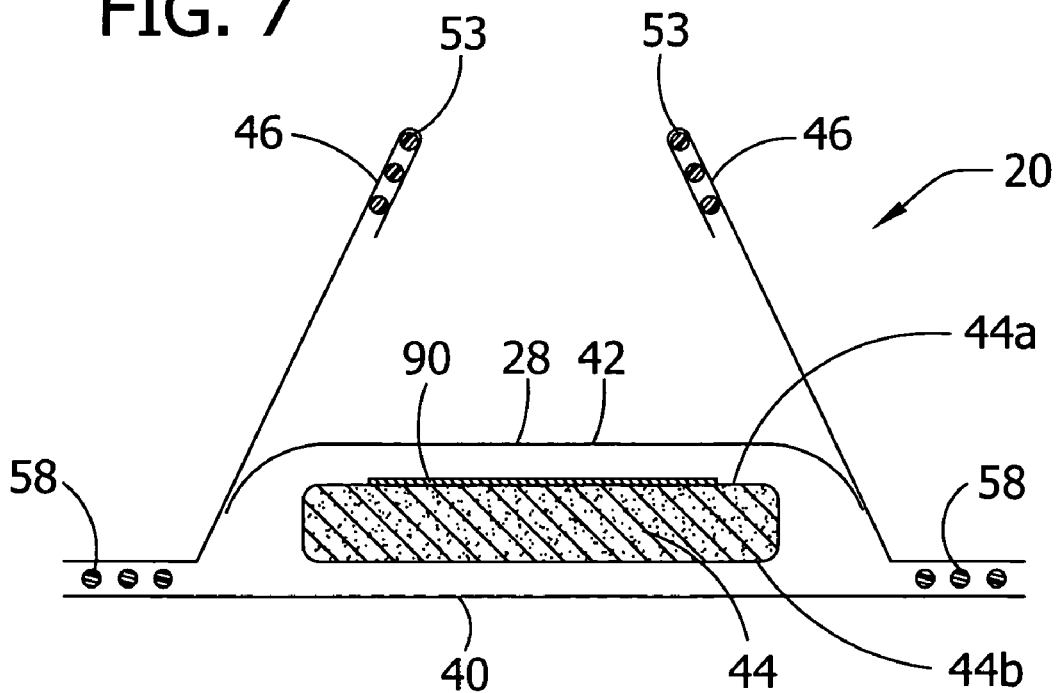

ABSORBENT ARTICLE HAVING AN INTERIOR GRAPHIC

FIELD OF THE INVENTION

The present invention relates generally to absorbent articles intended for personal wear, and more particularly to an absorbent article having an interior graphic and a process for manufacturing such an absorbent article.

BACKGROUND OF THE INVENTION

Absorbent articles such as diapers, training pants, incontinence garments, and the like conventionally include a liquid permeable body-facing liner, a liquid-impermeable outer cover, an absorbent core (also referred to as an absorbent body or absorbent structure), and in some instances, graphics visible on the exterior surface of the article. The graphics may provide a decorative feature, and particularly when used in connection with children's training pants, may be used to make the pants appear similar to conventional underwear. Further, the graphics may also be used to encourage training and/or be used to make the training experience more enjoyable and a generally positive experience. For example, the graphics may be used to allow the caregiver to interact with the wearer in the training setting.

Accordingly, the graphics may take various forms, such as in the form of a character, object and/or alphanumeric (e.g., numbers, words, phrases, instructions, etc.), and the like. Moreover, at least some of the graphics may be "active graphics" configured to be capable of appearing or disappearing when the article is exposed to liquid, such as urine. These graphics can alert the wearer and the caregiver to the occurrence of urine in the article (i.e., an "accident"), and can assist in the training process. Reference may be made to U.S. Pat. No. 6,297,424, incorporated by reference herein for all purposes, for additional background information regarding graphics visible on the external surface of the article.

Nonetheless, such graphics, in certain circumstances, may not be completely satisfactory. For example, in some configurations, appearing or disappearing graphics visible on the exterior of the article may require a considerable amount of liquid, or multiple accidents, before the graphics are caused to appear or disappear. Additionally, graphics visible on the exterior of the article do not necessarily motivate the wearer to pull the article up and down for inspection, which can be a key training step.

There is a need, therefore, to provide a suitable training tool that can help notify the wearer of any accidents, even if the accident is relatively small in volume. In addition, there is a need for a training tool that encourages the wearer to practice pulling the article up and down to check the status of a graphic visible from the bodyside of the absorbent article. Further, there is a need for a training tool that has a graphic visible from the bodyside of the absorbent article that does not bleed onto the skin of the wearer.

Furthermore, a need exists to reduce capital costs by more efficiently utilizing space on the manufacturing room floor and more efficiently incorporating the process for printing the graphics into the existing process for manufacturing the absorbent article.

SUMMARY OF THE INVENTION

In one aspect, the present invention is directed generally to an absorbent article having an inner surface adapted to be disposed toward a wearer of the article and an outer surface opposite said inner surface. An outer cover at least in part defines the outer surface of the article and a liner in opposed relationship with the outer cover at least in part defines the inner surface of the article. An absorbent structure is disposed between the liner and the outer cover. At least one graphic is disposed intermediate the inner surface and the outer surface of the article and is free from direct contact with the liner. The article is configured such that the graphic is visible from the inner surface of the article.

In another aspect, the present invention is directed generally to a process for manufacturing an absorbent article having an outer cover at least in part defining the outer surface of the article, a liner at least in part defining the inner surface of the article, an absorbent structure disposed between the outer cover and liner, and at least one graphic intermediate the outer cover and liner and visible from the inner surface of the article. The process comprises arranging the absorbent structure between the liner and the outer cover. The liner is secured to the outer cover. At least one graphic is applied to the article intermediate the outer cover and liner. The graphic is free from direct contact with the liner and visible from the inner surface of the article.

In yet another aspect, the present invention is directed generally to a process for manufacturing an absorbent article having at least one graphic visible from the interior of the article. The process comprises positioning an absorbent structure between a liner and an outer cover with the liner and outer cover in generally opposed relationship with each other. A surge layer is arranged between the absorbent structure and the liner and a wrapsheet surrounds the surge layer and at least a portion of the absorbent structure. The liner is secured to the outer cover. At least one graphic is applied to the article intermediate the outer cover and the liner and is visible through the liner.

Other features of the invention will be in part apparent and in part pointed out hereinafter.

BRIEF DESCRIPTION OF THE DRAWINGS

FIG. 4 is a section view taken along the plane including line 4-4 of FIG. 3 showing the placement of a graphic visible from the inner surface of the article;

FIG. 5 is a section view similar to FIG. 4 but showing an alternative placement of the graphic;

FIG. 6 is a section view similar to FIG. 4 but showing an alternative placement of the graphic;

FIG. 7 is a section view similar to FIG. 4 but showing an alternative placement of the graphic;

Corresponding reference characters indicate corresponding parts throughout the drawings.

DETAILED DESCRIPTION

Figure 1:
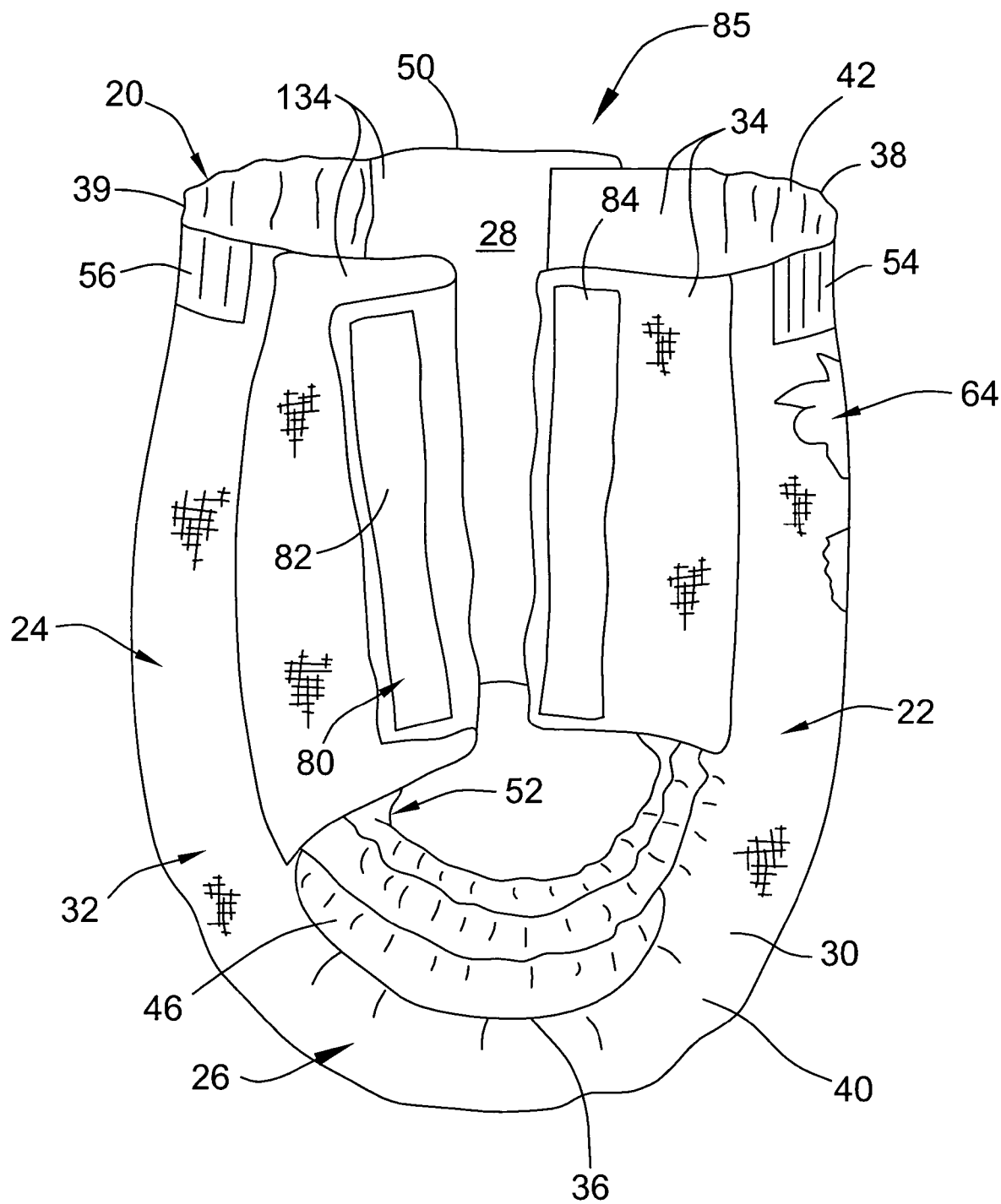
FIG. 1 is a side perspective of an article of the present invention shown in the form of a pair of training pants having a mechanical fastening system fastened on one side of the training pants and unfastened on the opposite side thereof.

Referring now to the drawings and in particular to FIG. 1, an absorbent article of the present invention is representatively illustrated therein in the form of children's toilet training pants and is indicated in its entirety by the reference numeral 20. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants such as the pants 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference.

Figure 2:
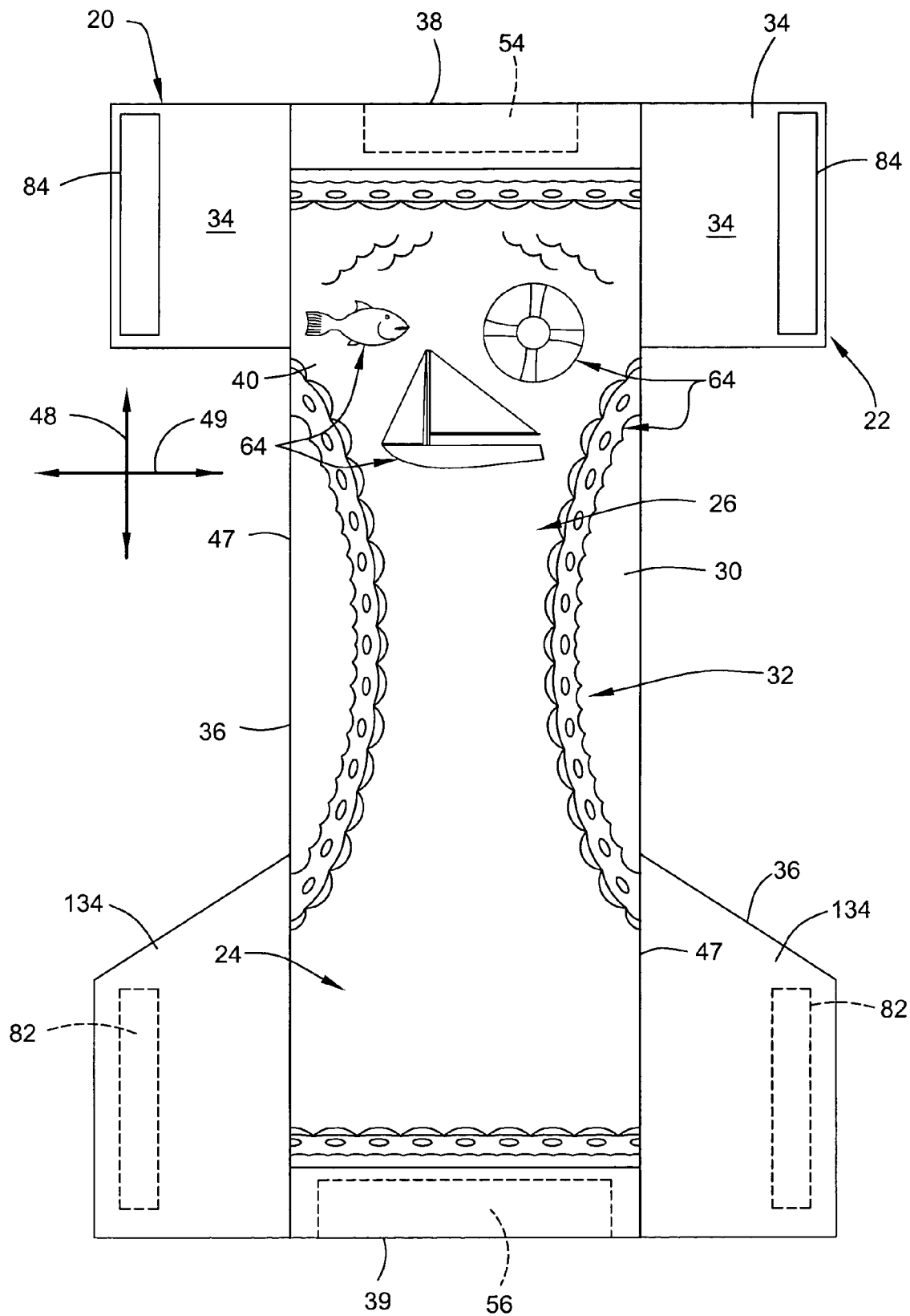
FIG. 2 is a bottom plan view of the training pants of FIG. 1 with the pants in an unfastened, unfolded and laid flat condition, and showing the surface of the training pants that faces away from the wearer.
Figure 3:
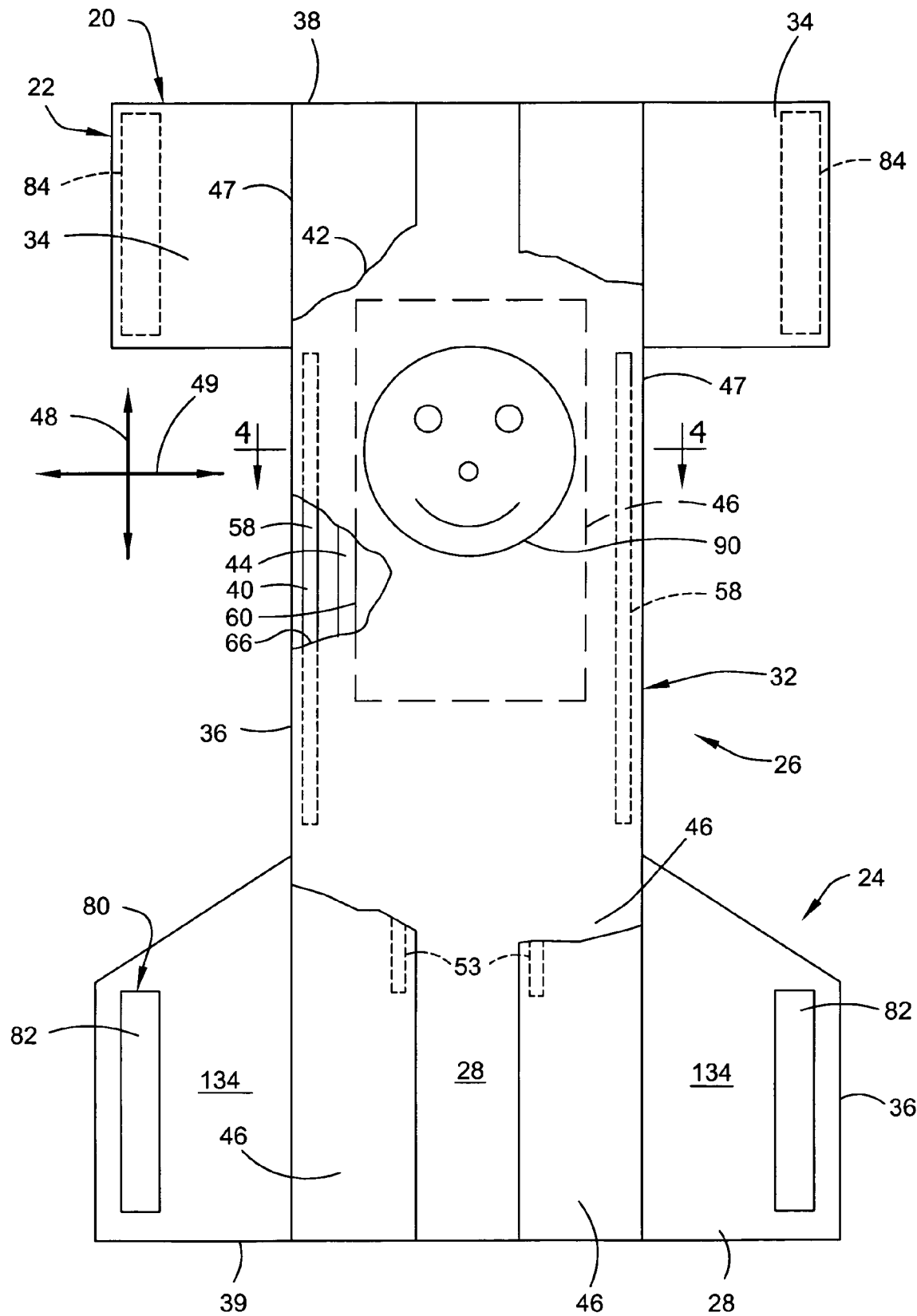
FIG. 3 is a top plan view similar to FIG. 2 showing the inner surface of the training pants that faces the wearer when worn and with portions cut away to show underlying features.

The pair of training pants 20 is illustrated in FIG. 1 in a partially fastened condition. The pants 20 define a longitudinal direction 48 of the pants (e.g. of the article) and a lateral direction 49 thereof perpendicular to the longitudinal direction as shown in FIGS. 2 and 3. The pants 20 further define a pair of longitudinal end regions, otherwise referred to herein as a front waist region 22 and a back waist region 24, and a center region, otherwise referred to herein as a crotch region 26, extending longitudinally between and interconnecting the front and back waist regions 22, 24. The pants 20 also define an inner surface 28 adapted in use (e.g., positioned relative to the other components of the pants 20) to be disposed toward the wearer, and an outer surface 30 opposite the inner surface. The front and back waist regions 22, 24 comprise those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. With additional reference to FIGS. 2 and 3, the pair of training pants 20 has a pair of laterally opposite side edges 36 and a pair of longitudinally opposite waist edges (broadly, longitudinal ends), respectively designated front waist edge 38 and back waist edge 39.

The illustrated pants 20 comprises an absorbent assembly, generally indicated at 32, and a fastening system for securing the pants in a three-dimensional pants configuration. In the embodiment of FIGS. 1-3, the training pants 20 comprises a generally rectangular central absorbent assembly 32 and side panels 34, 134 formed separately from and secured to the central absorbent assembly. The side panels 34, 134 are permanently bonded along seams 66 to the central absorbent assembly 32 in the respective front and back waist regions 22 and 24 of the pants 20. More particularly, the front side panels 34 can be permanently bonded to and extend transversely outward beyond side margins 47 of the absorbent assembly 32 at the front waist region 22, and the back side panels 134 can be permanently bonded to and extend transversely outward beyond the side margins of the absorbent assembly at the back waist region 24. The side panels 34 and 134 may be bonded to the absorbent assembly 32 using attachment means known to those skilled in the art such as adhesive, thermal or ultrasonic bonding.

The front and back side panels 34 and 134, upon wearing of the pants 20, thus comprise the portions of the training pants 20 which are positioned on the hips of the wearer. The front and back side panels 34 and 134 can be permanently bonded together to form the three-dimensional configuration of the pants 20, or be releasably connected with one another such as by the fastening system 80 of the illustrated aspects.

In the embodiment of FIGS. 1-3, the side panels 34, 134 comprise an elastic material capable of stretching at least in a direction generally parallel to the lateral direction 49 of the training pants 20. Suitable elastic materials, as well as one process of incorporating elastic side panels into training pants, are described in the following U.S. patents: U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. Alternatively, the side panel material may include other woven or non-woven materials, such as those described herein as being suitable for construction of the outer cover 40 and/or the bodyside liner 42; mechanically pre-strained composites; or stretchable but inelastic materials.

The absorbent assembly 32 is illustrated in FIGS. 1-3 as having a rectangular shape. However, it is contemplated that the absorbent assembly 32 may have other shapes (e.g., hourglass, T-shaped, I-shaped, and the like) without departing from the scope of this invention.

The absorbent assembly 32 comprises an outer cover 40 and a bodyside liner 42 (FIGS. 1 and 3) attached to the outer cover 40 in a superposed (opposed) relation therewith by adhesives, ultrasonic bonds, thermal bonds, pressure bonds, or other conventional techniques. The liner 42 is suitably joined to the outer cover 40 along at least a portion of the longitudinal ends of the pants 20. In addition, the liner 42 is suitably joined to the outer cover 40. The liner 42 is suitably adapted, i.e., positioned relative to the other components of the pants 20, for contiguous relationship with the wearer's skin during wear of the pants. The absorbent assembly 32 also comprises an absorbent structure 44 (FIG. 3) disposed between the outer cover 40 and the bodyside liner 42 for absorbing liquid body exudates exuded by the wearer and a pair of containment flaps 46 secured to the bodyside liner 42 for inhibiting the lateral flow of body exudates.

With the training pants 20 in the fastened position as partially illustrated in FIG. 1, the front and back waist regions are connected together by the fastening system 80 to define the three-dimensional pants configuration having a waist opening 50 and a pair of leg openings 52. The front and back waist edges 38 and 39 (e.g. longitudinal ends) of the training pants 20 are configured to encircle the waist of the wearer to define the waist opening 50 (FIG. 1) of the pants.

As illustrated in FIG. 3, a flap elastic member 53 can be operatively joined with each containment flap 46 in any suitable manner as is well known in the art. The elasticized containment flaps 46 define a partially unattached edge which assumes an upright configuration in at least the crotch region 26 of the training pants 20 to form a seal against the wearer's body. The containment flaps 46 can be located along the side edges, and can extend longitudinally along the entire length of the absorbent assembly 32 or may extend only partially along the length thereof. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may comprise a front waist elastic member 54 (FIG. 2), a rear waist elastic member 56, and leg elastic members 58 (FIG. 3), as are known to those skilled in the art. The waist elastic members 54 and 56 may be operatively joined to the outer cover 40 and/or the bodyside liner 42 adjacent the longitudinal ends 38, 39. The leg elastic members 58 may be operatively joined to the outer cover 40 and/or the bodyside liner 42 along the opposite side edges generally at the crotch region 26 of the training pants 20.

The flap elastic members 53, the waist elastic members 54 and 56, and the leg elastic members 58 can be formed of any suitable elastic material. As is well known to those skilled in the art, suitable elastic materials comprise sheets, threads, strands, or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may comprise a plurality of dry-spun coalesced multifilament spandex elastomeric threads sold under the trade name LYCRA and available from Invista, Inc. of Wilmington, Del., U.S.A.

The fastening system 80 of the illustrated embodiment comprises laterally opposite first fastening components 82 adapted for refastenable engagement to corresponding laterally opposite second fastening components 84. In one embodiment, a front or outer surface of each of the fastening components 82, 84 comprises a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 comprise loop fasteners and the second fastening components 84 comprise complementary hook fasteners. Alternatively, the first fastening components 82 can comprise hook fasteners and the second fastening components 84 can comprise complementary loop fasteners. In another embodiment, the fastening components 82, 84 can comprise interlocking similar surface fasteners, or adhesive and cohesive fastening elements such as an adhesive fastener and an adhesive-receptive landing zone or material, or the like. One skilled in the art will recognize that the shape, density and polymer composition of the hooks and loops may be selected to obtain the desired level of engagement between the fastening components 82, 84. When engaged, the fastening components 82, 84 of the illustrated aspect define refastenable engagement seams 85 (FIG. 1). Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

The outer cover 40 suitably comprises a material that is substantially liquid impermeable. The outer cover 40 can be a single layer of liquid impermeable material, but more suitably comprises a multi-layered laminate structure in which at least one of the layers is liquid impermeable. For instance, the outer cover 40 can comprise a liquid permeable outer layer and a liquid impermeable inner layer that are suitably joined together by a laminate adhesive, ultrasonic bonds, thermal bonds, pressure bonds or the like. Suitable laminate adhesives, which can be applied continuously or intermittently as beads, a spray, parallel swirls, or the like, can be obtained from Bostik Findley Adhesives, Inc., of Wauwautosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polyolefin nonwoven web. The outer layer may also be made of those materials of which the liquid permeable bodyside liner 42 is made. While it is not a necessity for the outer layer to be liquid permeable, it is suitable that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.75 mil (0.02 millimeter) polyethylene film commercially available from Pliant Corporation of Schaumburg, Ill., U.S.A.

Optionally, the outer cover 40 may be stretchable, and in some embodiments it may be elastomeric. As used herein, the term "stretchable" refers to a material that may be extensible or elastomeric. That is, the material may be extended, deformed or the like, without breaking, and may or may not significantly retract after removal of an extending force. The terms "elastomeric" or "elastic" are used interchangeably herein and refer to that property of a material where upon removal of an elongating force, the material is capable of recovering to substantially its unstretched size and shape or the material exhibits a significant retractive force. The term "extensible" refers to that property of a material where upon removal of an elongating force, the material experiences a substantially permanent deformation or the material does not exhibit a significant retractive force. In particular, elastomeric materials utilized in connection with the present invention may be elongated/extended or stretched in at least one direction without breaking by at least 25% (to at least 125% of its initial unstretched length) in at least one direction, suitably by at least 50% (to at least 150% of its initial unstretched length) and which will recover, upon release of the applied stretching or biasing force, at least 10% of their elongation. It is generally preferable that the elastomeric material or composite be capable of being elongated by at least 100%, more preferably by at least 200%, of its relaxed length and recover at least 30% and more preferably 50% of its elongation upon release of a stretching, biasing force, within about one minute.

Similarly, extensible or elongatable materials of the present invention may be capable of stretching in at least one direction without breaking by at least 25% (to at least 125% of its initial unstretched length) in at least one direction, suitably by at least 50% (to at least 150% of its initial unstretched length), more suitably by at least 100% (to at least 200% of its initial unstretched length). As an example, an extensible material having an initial unstretched length of 3 inches (7.6 centimeters) may be stretched without breaking to a stretched length of at least 3.75 inches (9.5 centimeters) in at least one direction (for the "by at least 25%" value).

The outer cover 40 may be constructed of spunbond fabrics, films, meltblown fabrics, elastic netting, microporous web, bonded carded webs or foams provided by elastomeric or polymeric materials. Elastomeric non-woven laminate webs can comprise a non-woven material joined to one or more gatherable non-woven webs, films, or foams. Stretch Bonded Laminates (SBL) and Neck Bonded Laminates (NBL) are examples of elastomeric composites. Non-woven fabrics are any web of material that has been formed without the use of textile weaving processes which produce a structure of individual fibers that are interwoven in an identifiable repeating manner.

Examples of suitable materials are spunbond-meltblown fabrics, spunbond-meltblown-spunbond fabrics, spunbond fabrics, or laminates of such fabrics with films, foams, or other nonwoven webs. Elastomeric materials may include cast or blown films, foams, or meltblown fabrics composed of polyethylene, polypropylene, or polyolefin copolymers, as well as combinations thereof. The elastomeric materials may include PEBAX elastomer (available from AtoChem located in Philadelphia, Pa.), HYTREL elastomeric polyester (available from Invista, Inc. of Wilmington, Del.), KRATON elastomer (available from Kraton Polymers of Houston, Tex.), or strands of LYCRA elastomer (available from Invista, Inc. of Wilmington, Del.), or the like, as well as combinations thereof. The outer cover 40 may comprise materials that have elastomeric properties through a mechanical process, printing process, heating process, or chemical treatment. For example such materials may be apertured, creped, necked-stretched, heat activated, embossed, micro-strained, or combinations thereof and may be in the form of films, webs, and laminates.

In particular suitable embodiments of the invention, the outer cover 40 may include a 0.4 ounces per square yard (osy) (13.6 grams per square meter (gsm)) basis weight layer of G2760 KRATON elastomer strands adhesively laminated with a 0.3 gsm layer of adhesive between two facings. Each facing can be composed of a thermal point bonded bicomponent spunbond non-woven fibrous web having a 0.7 osy (23.7 gsm) basis weight. The adhesive is similar to an adhesive which is supplied by Bostik-Findley Adhesive of Wauwautosa, Wis. and designated as H2525 A, and the elastomer strands are placed and distributed to provide approximately 12 strands of KRATON elastomer per inch (2.54 cm) of lateral width of the outer cover 40.

Alternatively, the outer cover 40 may comprise a woven or non-woven fibrous web layer that has been totally or partially constructed or treated to impart the desired levels of liquid impermeability to selected regions that are adjacent or proximate the absorbent structure. For example, the outer cover 40 may include a gas-permeable, non-woven fabric layer laminated to a polymer film layer which may or may not be gas-permeable. Other examples of fibrous, cloth-like outer cover 40 materials can include a stretch thinned or stretch thermal laminate (STL) material composed of a 0.6 mil (0.015 mm) thick polypropylene blown film and a 0.7 osy (23.8 gsm) polypropylene spunbond material (2 denier fibers).

Suitable materials for a biaxially stretchable (i.e., stretchable both laterally and longitudinally) outer cover 40 include biaxially extensible material and biaxially elastic material. One example of a suitable biaxially stretchable outer cover material can include a 0.3 osy polypropylene spunbond that is necked 60% in the lateral direction 49 and creped 60% in the longitudinal direction 48, laminated with 3 grams per square meter (gsm) Bostik-Findley 2525A styrene-isoprene-styrene based adhesive to 8 gsm PEBAX 2533 film with 20% $TiO_2$ concentrate. The outer cover 40 can preferably be stretched, laterally and/or longitudinally, by at least 30% (to at least 130% of an initial (unstretched) width and/or length of the outer cover 40). More suitably, the outer cover 40 can be stretched laterally and/or longitudinally, by at least 50% (to at least 150% of the unstretched width or length of the outer cover 40). Even more suitably, the outer cover 40 can be stretched, laterally and/or longitudinally, by at least 100% (to at least 200% of the unstretched width or length of the outer cover 40). Tension force in the outer cover 40 at 50% extension is preferably between 50 and 1000 grams, more preferably between 100 and 600 grams, as measured on a 3 inch (7.62 cm) wide piece of the outer cover material.

Another example of a suitable material for a biaxially stretchable outer cover 40 is a breathable elastic film/nonwoven laminate, described in U.S. Pat. No. 5,883,028, issued to Morman et al., incorporated herein by reference. Examples of materials having two-way stretchability and retractability are disclosed in U.S. Pat. No. 5,116,662 issued to Morman and U.S. Pat. No. 5,114,781 issued to Morman, both of which are hereby incorporated herein by reference. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

The outer cover 40 is suitably sized (e.g., in length and width) larger than the absorbent structure 44 to extend outward beyond the periphery thereof. For example, the outer cover 40 may extend outward beyond the absorbent structure periphery a distance in the range of about 1.3 centimeters to about 2.5 centimeters (about 0.5 to 1 inch). Alternatively, the outer cover 40 may extend a greater amount or a lesser amount beyond the periphery of the absorbent structure 44 as is known in the art.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may comprise a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The bodyside liner 42 may also be stretchable, and more suitably it may be elastomeric. Suitable elastomeric materials for construction of the bodyside liner 42 can include elastic strands, LYCRA elastics, cast or blown elastic films, non-woven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers.

As an additional example, in one aspect the bodyside liner 42 suitably comprises a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) are adhered to the necked spunbond material. The fabric is surface treated with an operative amount of surfactant, such as about 0.6 percent AHCOVEL Base N62 surfactant, available from ICI Americas, a business having offices in Wilmington, Del., U.S.A. The surfactant can be applied by any conventional means, such as spraying, printing, brush coating or the like. Other suitable materials can be extensible biaxially stretchable materials, such as a neck stretched/creped spunbond. The bodyside liner 42 can also be made from extensible materials as are described in U.S. patent application Ser. No. 09/563,417 filed on May 3, 2000 by Roessler et al. or from biaxially stretchable materials as are described in U.S. patent application Ser. No. 09/698,512 filed on Oct. 27, 2000 by Vukos et al., both references which are herby incorporated by herein by reference.

The liner 42 can suitably be stretched, laterally and/or longitudinally, by at least 30% (to at least 130% of an initial (unstretched) width and/or length of the liner 42). More suitably, the liner 42 can be stretched laterally and/or longitudinally, by at least 50% (to at least 150% of the unstretched width or length of the liner 42). Even more suitably, the liner 42 can be stretched, laterally and/or longitudinally, by at least 100% (to at least 200% of the unstretched width or length of the liner 42). Tension force in the liner 42 at 50% extension is preferably between 50 and 1000 grams, more preferably between 100 and 600 grams, as measured on a 3 inch (7.62 cm) wide piece of the liner material.

The absorbent structure 44 is disposed between the outer cover 40 and the bodyside liner 42, which can be joined together by any suitable means such as adhesives, ultrasonic bonds, thermal bonds, or the like. While the illustrated absorbent structure 44 is shown and described herein as extending from the crotch region 26 into both the front and back waist regions 22 and 24, it is contemplated that the absorbent structure may extend from the crotch region into only the front waist region, or only the back waist region, without departing from the scope of this invention.

The absorbent structure 44 is suitably compressible, conformable, non-irritating to a wearer's skin, and capable of absorbing and retaining liquids and certain body wastes. For example, the absorbent structure 44 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent structure comprises a matrix of cellulosic fluff and superabsorbent hydrogel-forming particles. The cellulosic fluff may include a blend of wood pulp fluff. One suitable type of fluff is identified with the trade designation CR 1654, available from U.S. Alliance of Childersburg, Ala., USA, and is a bleached, highly absorbent sulfate wood pulp containing primarily soft wood fibers.

The materials may be formed into a web structure by employing various conventional methods and techniques. For example, the absorbent structure 44 may be formed by a dry-forming technique, an air forming technique, a wet-forming technique, a foam-forming technique, or the like, as well as combinations thereof. Methods and apparatus for carrying out such techniques are well known in the art. Furthermore, the absorbent structure 44 may itself encompass multiple layers in a Z-direction (e.g., thickness) of the absorbent structure. Such multiple layers may take advantage of differences in absorbent capacity, such as by placing a lower absorbent capacity material layer and/or a surge-type material closer to the liner 42 and a higher absorbent capacity material closer to the outer cover 40. Likewise, discrete portions of a single-layered absorbent structure may encompass higher capacity absorbents, and other discrete portions of the structure may encompass lower capacity absorbents.

Superabsorbent material is suitably present in the absorbent structure 44 in an amount of from about 0 to about 90 weight percent based on total weight of the absorbent structure. The absorbent structure 44 may suitably have a density within the range of about 0.10 to about 0.35 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid. Suitable superabsorbent materials are readily available from various suppliers. For example, SXM 9394, and Favor 9543 are suitable superabsorbent materials available from Degussa Superabsorbers of Germany.

The absorbent structure 44 may alternatively comprise a coform material. The term "coform material" generally refers to composite materials comprising a mixture or stabilized matrix of thermoplastic fibers and a second non-thermoplastic material. As an example, coform materials are made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the meltspun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

In the preferred embodiment, the absorbent structure 44 is stretchable so as not to inhibit the stretchability of other components to which the absorbent structure may be adhered, such as the outer cover 40 and bodyside liner 42. In a particularly suitable embodiment, the bodyside liner 42, the outer cover 40, and the absorbent structure 44 are each stretchable so that the absorbent structure allows for increased stretchability of the absorbent article as a whole. That is, non-stretchable absorbent structures tend to inhibit stretching of the outer cover and liner, even where the outer cover and liner are stretchable. A stretchable absorbent structure allows the outer cover and liner to more readily stretch, thereby increasing the overall stretchability (and ease of stretching) the entire article.

For this purpose, the absorbent structure material can include elastomeric fibers in an amount which is at least a minimum of about 2 wt %. The amount of elastomeric fibers can alternatively be at least about 3 wt %, and can optionally be at least about 5 wt % to provide improved performance. In addition, the amount of elastomeric fibers can be not more than about 60 wt %. Alternatively, the amount of elastomeric fibers can be not more than about 45 wt %, and optionally, can be not more than about 30 wt % to provide improved benefits. The elastomeric fiber content may impact the absorbent structure 44 stretchability and structural stability without excessively degrading the physical properties or the liquid-management properties of the absorbent structure. An absorbent structure 44 comprising an excessively low proportion of elastomeric fibers may be insufficiently stretchable, and one with an excessively high proportion of elastomeric fibers may exhibit an excessive degradation of its absorbent characteristics, such as poor intake, poor distribution and poor retention of liquid.

The absorbent structure 44 in one particularly suitable embodiment comprises an elastomeric coform material. Such materials are described for instance in U.S. Pat. Nos. 6,231,557 B1 and 6,362,389 B1, which are each incorporated by reference herein. In particular aspects, the elastomeric coform material can have an overall coform basis weight which is at least a minimum of about 50 g/m². The coform basis weight can alternatively be at least about 100 g/m² and can optionally be at least about 200 g/m² to provide improved performance. These values can provide the absorbent structure 44 with the desired stretchability and structural stability without excessively degrading the physical properties or the liquid-management characteristics of the absorbent structure.

Other examples of suitable elastomeric absorbent structures are described in international patent application WO 03/051254 and U.S. Pat. Nos. 5,964,743, 5,645,542, 6,231,557, and 6,362,389 B1, each of which are incorporated by reference herein.

In some embodiments, such as that shown in FIG. 6, a surge management layer 60 is located adjacent the absorbent structure 44 (e.g., between the absorbent structure and the liner 42) and attached to various components of the article 20 such as the absorbent structure and/or the bodyside liner 42 by methods known in the art, such as by adhesive, ultrasonic or thermal bonding. A surge management layer 60 helps to decelerate and diffuse surges or gushes of liquid that may be rapidly introduced into the absorbent structure 44 of the article 20. Desirably, the surge management layer 60 can rapidly accept and temporarily hold the liquid prior to releasing the liquid into the storage or retention portions of the absorbent structure 44. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein.

It is also contemplated that a surge layer material may be formed integrally with the absorbent structure 44, such as during initial air forming/air laying or other forming of the absorbent structure. For example, fibers deposited at the inner surface of the absorbent structure 44 may be different from those deposited throughout the remainder of the absorbent structure so that the inner surface defines an integrally formed surge layer.

Optionally, a substantially liquid permeable wrapsheet 66 may be employed to help maintain the integrity of the absorbent structure 44. The wrapsheet 66 is typically placed about the absorbent structure 44 over at least the two major facing surfaces thereof. The wrapsheet 66 may comprise a polymeric non-woven such as spunbound, SMS, or the like or an absorbent cellulosic material, such as creped wadding, a high wet-strength tissue, or other non-woven material. The wrapsheet 66 can also be configured to provide a wicking layer that helps to rapidly distribute liquid to the absorbent fibers within the absorbent structure 44. The wrapsheet material 66 on one side of the absorbent structure 44 may be bonded to the wrapsheet located on the opposite side of the fibrous mass to effectively entrap the absorbent structure. In the embodiment of FIGS. 3 and 4, the wrapsheet 66 encloses both the surge layer 60 and the absorbent structure 44. However, it will be understood that the article 20 may comprise an absorbent structure without a tissue wrapsheet 66 or the wrapsheet may only enclose the absorbent structure with the surge layer 60 attached to an outer surface of the wrapsheet.

As shown in FIGS. 3 and 4, the absorbent article 20 of the present invention comprises a graphic 90, in the form of a smiley face, that is visible from the inner surface 28 of the article. The graphic 90 comprises a layer of ink disposed below the body side liner 42 of the article so that the ink is not readily transferred from the article to the skin of the wearer. The graphic 90 of the present invention may be an active graphic or a combination of active and permanent graphics. Further, the absorbent article 20 may comprise more than one graphic 90 without departing from the scope of the invention. As used herein, the term "active graphic" refers to an appearing graphic, a fading graphic, or a combination of appearing and fading graphics. The term "appearing graphic" is used herein to refer to a graphic that becomes visible or becomes significantly more visible when exposed to urine, or that becomes visible or becomes significantly more visible with the passage of time when exposed to the environment but not exposed to urine. Conversely, the term "fading graphic" is used herein to refer to a graphic that becomes invisible or significantly less visible when exposed to urine, or that becomes invisible or significantly less visible with the passage of time when exposed to the environment but not exposed to urine. For example, when the wearer wets the training pant 20, liquid is communicated to the active graphic 90, whereupon the active graphic either dissolves, changes color, appears, or the like. Where appearing graphics are employed, the situation would work in reverse. Alternatively, the active graphic can comprise appearing graphics that are triggered upon use by exposure to the environment.

In one aspect, fading graphics of the present invention may be formed from an ink that is soluble in aqueous solutions such as urine. As such, the ink can be positioned in the pant 20 so that it becomes wet and dissolves when the product is insulted with liquid. Suitable urine-soluble inks are available from a variety of commercial vendors, such as Sun Chemical Corp. of Philadelphia, Pa., USA under the trade designation AQUA DESTRUCT. Particular urine-soluble compositions are disclosed in U.S. Pat. No. 4,022,211 issued May 10, 1977 to Timmons et al., which is incorporated herein by reference to the extent it is consistent (i.e., not in conflict) herewith. The ink color can be selected to provide a pleasing appearance and graphic impact, including fading rapidly upon contact with liquid. In particular aspects, and to facilitate rapid fading, the fading graphics can comprise line drawings having a line width of from about 1 to about 5 millimeters.

Alternatively, the active graphic can also comprise a fading or an appearing graphic which is formed from a composition such as an ink or adhesive that changes color when exposed to an aqueous solution such as urine. A color change composition can be adapted to blend in with a background or surrounding color, either before or after exposure to the aqueous solution. Suitable compositions of this color-change type are available from a variety of commercial vendors, such as a pH-change/color-change hot melt adhesive available from Bostik-Findley Adhesives, Inc. of Wauwatosa, Wis., USA. Alternatively, the active graphic can comprise pH sensitive inks, fugitive inks, colored absorbent particles, hydratable salts, moisture sensitive films, enzymes, heat sensitive inks and dyes, or the like.

In contrast to active graphics, the term "permanent graphic" is used herein to refer to a graphic that does not substantially change its degree of visibility when the absorbent article is insulted with urine in simulated use conditions. The change in visibility of a graphic or a portion of a graphic can be determined based on a person's observation of the graphic before and after the article containing the graphic is exposed to liquid. For purposes hereof, an article is exposed to liquid by immersing the article completely in an aqueous solution containing 0.9 weight percent sodium chloride, used at room temperature ($\cong 23°$ C.), for a period of twenty minutes. After 20 minutes the product is removed from the aqueous solution and placed on a TEFLON™ coated fiberglass screen having 0.25 inch (6.35 mm) openings, which is commercially available from Taconic Plastics Inc., Petersberg, N.Y., USA, which in turn is placed on a vacuum box and covered with a flexible rubber dam material. A vacuum of 3.5 kilopascals (0.5 pounds per square inch) is drawn in the vacuum box for a period of 5 minutes, after which the article is removed and observed. The person with normal or corrected vision of 20-20 should make the observations from a distance of 1 meter in an environment providing 30 footcandles (320 Lux) of illumination. Changes in the visibility of the graphic should be identified, and distinguished where necessary from changes in the color of other materials such as fluff pulp within an absorbent assembly. Desirably, the permanent graphic can be configured so that the entire graphic also does not substantially change its appearance, size or shape when the product is insulted with liquid or exposed to the environment.

The graphic 90 may include, but is not limited to, scenes, characters, animals, objects, alphanumerics such as numbers, letters, words, phrases and the like. In particular aspects, the graphic 90 may also be gender specific; that is, the graphic may be generally considered to be of interest to boys or to girls.

As shown in FIG. 4, the graphic 90 is printed on the bottom surface of a portion of the wrapsheet 66 disposed between the absorbent structure 44 and bodyside liner 42 so that the graphic is visible from the inner surface 28 of the article 20 but is otherwise out of direct contact with the liner. The graphic 90 may be placed on the pants 20 using a variety of methods. As an example, the graphics 90 may be imprinted on the wrapsheet 66 using a flexographic printing process. Flexographic printing is a conventional printing technique which uses flexible, raised rubber or photopolymer plates to carry an inked image to a substrate, such as the outer cover 40, liner 42, wrapsheet 66, surge layer 60, or absorbent structure 44. As an example, flexographic printing apparatus are shown and/or described in U.S. Pat. No. 5,458,590 (Schleinz et al.); U.S. Pat. No. 5,566,616 (Schleinz et al.); U.S. 2003/0019374A1 (Harte); and U.S. Pat. No. 4,896,600 (Rogge et al.). Further, the graphic 90 may be printed, sprayed, or otherwise applied to the absorbent article 20 by any other method (e.g., ink jet, rotogravure, etc.).

In the embodiment of FIG. 4, the graphic 90 is free from direct contact with the bodyside liner 42 so that the ink of the graphic is not easily transferred to the skin of the wearer by contact between the wearer and the inner surface 28 of the article 20. By preventing the transfer of ink between the training pants 20 and the body of the wearer, the graphic 90 is more effective as a training tool because the graphic remains clear when the wearer wets the article.

FIG. 5 shows an alternative embodiment of the absorbent article 20 similar to the previous embodiments but with the graphic 90 located on a liner-facing surface 60a of the surge layer 60. In the embodiment of FIG. 5, the graphic 90 is separated from the inner surface 28 of the article 20 by the wrapsheet 66 and the bodyside liner 42.

FIG. 6 shows an alternative embodiment of the absorbent article 20 similar to the previous embodiments but with the graphic 90 located on a cover-facing surface 60b of the surge layer 60. In the embodiment of FIG. 6, the graphic 90 is separated from the inner surface 28 of the article 20 by the surge layer 60, the wrapsheet 66 and the bodyside liner 42.

FIG. 7 shows an alternative embodiment of the absorbent article 20 similar to the previous embodiments but with the graphic 90 located on a liner-facing surface 44a of the absorbent structure 44. As shown in FIG. 7, the graphic is separated from the inner surface 28 of the article 20 by the bodyside liner 42. It will be understood that a wrapsheet 66 may enclose the absorbent structure 44 and graphic 90 of this embodiment so that the wrapsheet forms an additional intervening layer between the graphic and the inner surface 28 of the article 20.

Figure 8:
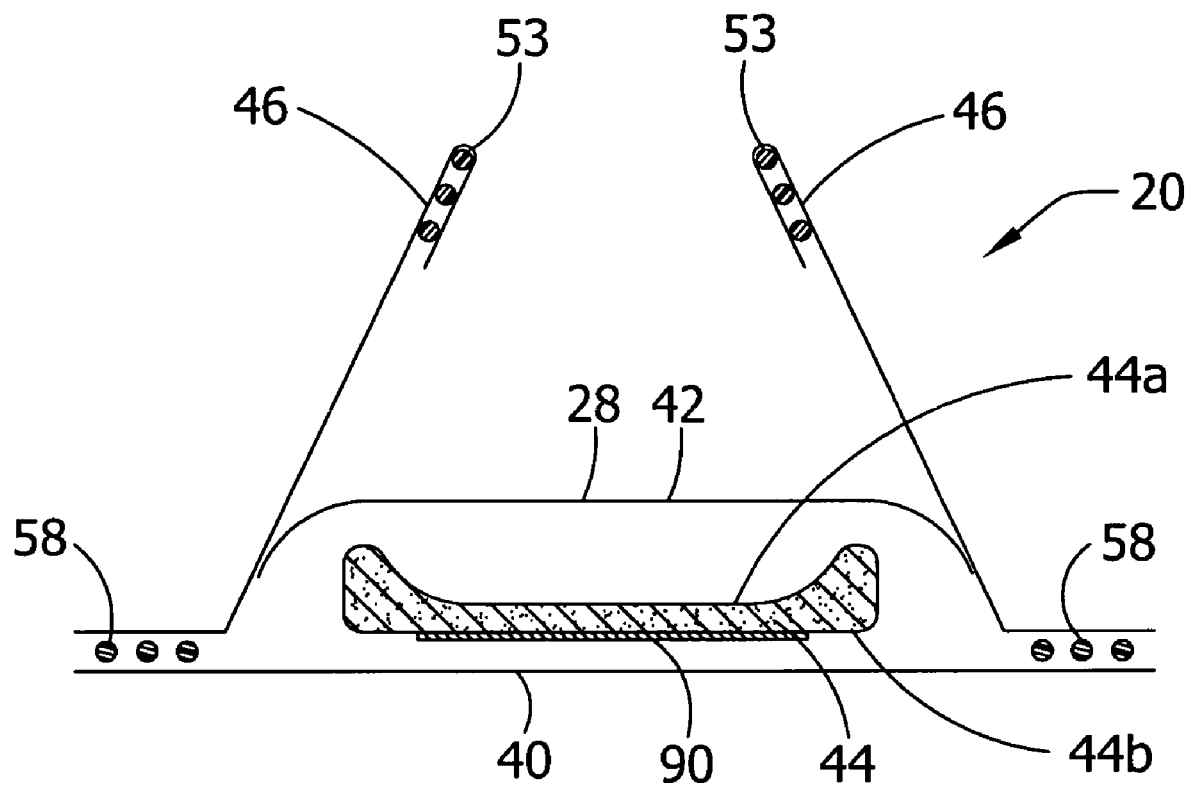
FIG. 8 is a section view similar to FIG. 4 but showing an alternative placement of the graphic.

FIG. 8 shows an alternative embodiment of the absorbent article 20 similar to the previous embodiments but with the graphic 90 located on a cover-facing surface 44b of the absorbent structure 44. As shown in FIG. 8, the graphic is separated from the inner surface 28 of the article 20 by the absorbent structure 44 and bodyside liner 42. As in the previous embodiment, a wrapsheet 66 may enclose the absorbent structure 44 and graphic 90 so that the wrapsheet forms an additional intervening layer between the graphic and the inner surface 28 of the article 20. The absorbent structure 44 of FIG. 8 has a central portion of reduced thickness at the location of the applied graphic 90 so that the absorbent structure is more translucent to thereby facilitate visibility of the graphic 90 from the inner surface 28 of the article 20. Alternatively, the materials from which the absorbent structure 44 is constructed may be modified by adding or omitting one or more additives (e.g., omitting a titanium dioxide additive) to render the absorbent structure more translucent and thereby increase the visibility of the graphic 90.

Preferably, the graphic 90 may appear or fade in about 3 minutes or less, more particularly in about 1 minute or less, and still more particularly in about 20 seconds or less, when the absorbent article 20 is insulted with 200 milliliters or more of urine, suitably when the absorbent article is insulted with about 40 to about 60 milliliters or more of urine, and more suitably when the absorbent article is insulted about 10 milliliters or more of urine.

In use, the graphic 90 visible to wearer of the article 20 from the inner surface 28 assists in toilet training of the wearer. For example, the graphic 90 can encourage the wearer to pull the pants 20 up and down to view the inner surface 28 of the article 20 and inspect the graphic 90, an activity which is a key to toilet training and requires a relatively high level of coordination. In addition, as can be readily appreciated a graphic 90 may encourage the wearer to refrain from wetting the article 20 in order to keep the graphic in place. Further, the graphic 90 can provide the wearer with a feeling of "ownership" over the graphic, as the graphic is intended primarily for their viewing. Still further, an active graphic 90 positioned to be viewed from the inner surface 28 of the article 20 is more sensitive to even small accidents than active graphics otherwise located due to their proximity to the target area. As such, active graphics can be particularly effective in late stage training.

In order to provide a proper focus on the graphic 90, the graphic may be particularly positioned within the pants 20. Moreover, in configurations where the graphic 90 is an active graphic, it may be positioned in a gender specific target zone for urination within the product; such positioning can increase the likelihood that the graphic 90 will be activated by an insult. As such, in the illustrated embodiment, at least a portion of the graphic 90 is spaced from the front waist edge 38 in the longitudinal direction 48 by between 25% and 50% of the article length. In another aspect, at least a portion of the graphic 90 can be spaced from the front waist edge 38 in the longitudinal direction 48 by between 35% and 60% of the article length.

Figure 3A:
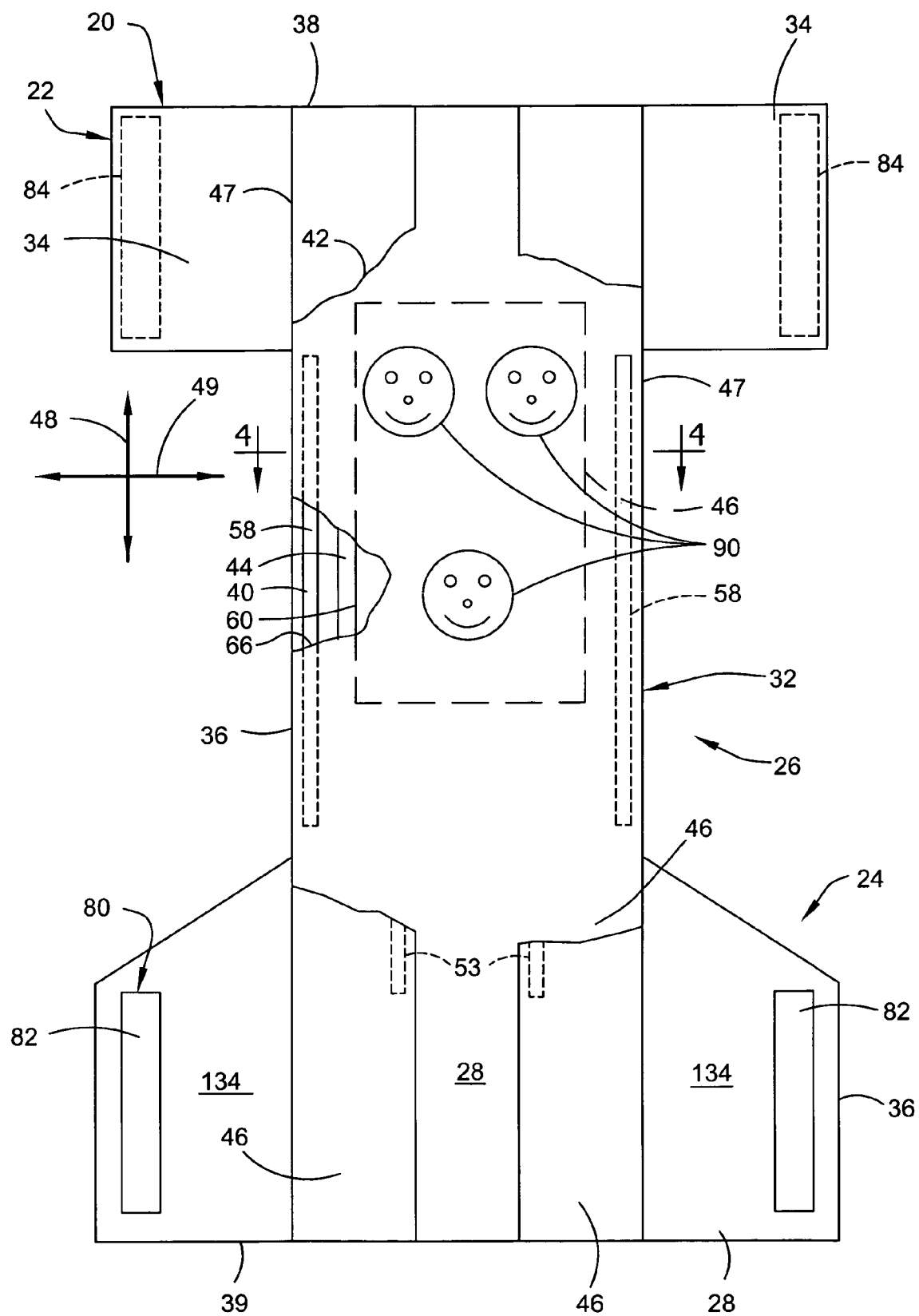
FIG. 3A is a view similar to FIG. 3 but showing an alternative embodiment of the training pants.

Moreover, each graphic 90 may define a total graphic area. In the illustrated embodiment, the total graphic area is equal to the area of the circular smiley face graphic 90 that may be calculated by squaring one-half of the diameter of the circle and multiplying by the constant pi (3.14). In other embodiments of the article 20, the graphic 90 may be generally rectangular or square and the total graphic area may be calculated by multiplying the largest dimension of the graphic in the longitudinal direction 48 by the largest dimension of the graphic 90 in the lateral direction 49. Preferably, the graphic area may be at least 25 square cm, or more preferably, the graphic area may be at least 45 square cm. Alternatively, as illustrated in FIG. 3A, the pants 20 may include a plurality of graphics 90. Thus, the plurality of graphics 90 may, in total, define a total graphic area. The total graphic area may be calculated by adding the graphic area of each graphic 90. The plurality of graphics 90 may define a total graphic area of at least 25 square cm. Such total graphic areas as described above suitably draws the attention of the wearer and can therefore act as a more meaningful training aid.

As shown in FIGS. 1 and 2, the training pants 20 includes at least one exterior graphic 64 disposed on the exterior article surface 30. In the illustrated embodiment, the pants 20 includes a plurality of exterior graphics 64. The exterior graphics 64 may include, but are not limited to, scenes, characters, animals, objects, alphanumerics such as numbers, letters, words, phrases and the like, highlighting or emphasizing leg and waist openings 52, 50 in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The exterior graphics 64 are formed on or applied to the outer cover 40 or another substrate bonded to or placed with or placed near the outer cover 40 by any suitable technique. The exterior graphics 64 are suitably registered with other components of the absorbent article 20 during manufacture such that the exterior graphics are positioned in the desired regions of the product.

The exterior graphics 64 may be active graphics, permanent graphics, or combinations thereof. In particular aspects, at least one of the exterior graphics 64 is an active graphic, and more particularly a fading graphic. Exterior graphics 64 suitable for use with the present invention are described in U.S. Pat. No. 6,297,424 issued Oct. 2, 2001 to Olson, et al. and U.S. Pat. No. 6,307,119 issued Oct. 23, 2001 to Cammarota et al., the disclosures of which are incorporated herein to the extent they are consistent (i.e., not in conflict) herewith.

The exterior graphics 64 of the present invention may also be configured to define a graphic theme. It should be noted that in order to establish a graphic theme, not every exterior graphic 64 need be directly related to the graphic theme, however, it can be appreciated that to effectively establish a graphic theme, it is desirable to have at least half of the exterior graphics 64 contribute to defining the graphic theme, more desirably the majority of the exterior graphics 64 contribute to defining the graphic theme, and still more desirably substantially all of the exterior graphics 64 contribute to defining the graphic theme. Similarly, it can be appreciated that where certain exterior graphics 64 are not contributing to defining the theme of the other exterior graphics 64, it can be most effective to at least have the non-contributing exterior graphics 64 be neutral or not in opposition toward the graphic theme.

The exterior graphics 64 may define a graphic theme when the subject matter of one exterior graphic is the same as or is associated with the subject matter of another exterior graphic. For example, the exterior graphics 64 may be related by a unifying subject or common story line, which could be generally known through books, movies, common children's activities, or other sources to provide a graphic theme. By way of example, two objects are considered the same as or associated in subject matter where the images are identical; separately illustrate different sizes, shapes, colors of a common object; each illustrate one and the other of two objects that are commonly associated with one another, such as the moon and stars, a body of water and water toys, a sandbox and suitable toys, a baseball bat and ball, a barn and animals, or the like; illustrate different items used in a particular activity, such as a sporting activity, a gardening activity or the like; jointly illustrate geometrically mating or engaging elements such as a triangle and a triangularly-shaped aperture, or two halves of a zipper; each illustrate one part of a multipart picture; or the like. Similarly, two text messages are considered related in subject matter where the messages: are identical; jointly form a sentence, thought, or action such as "jump" and "up"; each refer to one and the other of two items that are commonly associated with one another, such as "bat" and "ball," "Big" and "Kid," "Big" and "Girl," or "Big" and "Boy"; jointly present a question and answer; or the like. Likewise, a text message and a pictorial image are considered to be related in subject matter where the text names, defines or describes the image; or the like.

Conversely, and by way of illustration and without wishing to be limited to the enumerated examples, two objects are considered unrelated in subject matter where the images: illustrate items that are neither identical nor illustrate two objects that are not commonly associated with one another, such as an animal and a building block, a jump rope and a flower, a car and a star, a letter of the alphabet and a water toy, a fish and an apple, illustrate items used in unrelated activities, such as items used in sporting activities and items used in gardening activities, or other unrelated activities; or the like. Similarly, two text messages are considered unrelated in subject matter where the messages: are neither identical nor jointly form a sentence, thought, or action; refer to two items that are not commonly associated with one another, such as "ball" and "flower," "fish" and "pencil," "car" and "ghost," or other such unrelated words; or the like. Likewise, a text message and a pictorial image are considered to be unrelated in subject matter where the text does not name, define, describe or otherwise relate to the image.

Thus, the interior graphic 90 may be related or unrelated to a graphic theme that may be defined by the exterior graphics 64. Suitably, the interior graphic 90 may be related to the graphic theme. In particular, and without wishing to be limited to the specific embodiments listed, suitable examples of a graphic theme with a related interior graphic 90 can include: the exterior graphics 64 being a racquet, bat, glove, other sporting equipment or the like and the interior graphic 90 comprising balls, or being related sporting equipment or the like; the exterior graphics 64 being a butterfly net or the like and the interior graphics 90 comprising butterflies or the like; the exterior graphics 64 being a fish, a boat or the like and the interior graphic 90 being a shell, water toys or the like; the exterior graphics 64 being flowers, plants, gardening tools or the like and the interior graphic 90 comprising flowers or plants; the exterior graphics 64 being a specific environment such as a barn, silo, tractor or the like and the interior graphic 90 comprising cows, chickens, sheep, or the like which are specifically adapted to the environment; the exterior graphic 64 being a telescope, stars, planets or the like and the interior graphic 90 being rockets, spaceships or flying saucers.

In aspects where the interior graphic 90 is related to a theme established by the exterior graphics 64, it provides an opportunity for the wearer and the caregiver to interact and can improve the toilet training experience. For example, in one aspect the theme established by the exterior graphics 64 can include graphic that cannot complete some action or observation after a fading interior graphic 90 has disappeared. This facilitates nonthreatening and gentle communications between the wearer and caregiver when the child has had an accident and wet his or her pants. A caregiver might take a positive approach: "Try not to wet in your pants so the bear at the beach still has his sand toys to play with." Significantly this can be used as a motivational basis for teaching the child that it is within their control to permit the activity to continue for as long as the child can go without wetting his or her pants.

As mentioned above, the exterior graphics 64 and the interior graphics 90 may be disposed on the pants 20 using a variety of methods. For example, the graphics 64 and 90 may suitably be disposed on the pants 20 by being imprinted thereon using a flexographic printing process.

As noted previously, liquid soluble inks can be used to form the active graphics. It is theorized that the migration of the dissolved inks away from the surface upon which they are printed (for example, a surface of the outer cover 40, liner 42, absorbent structure 44, wrapsheet 66, surge layer 60, or combinations thereof) and into the absorbent structure 44 can improve the fading or disappearing quality of the active graphics. To enhance this effect, the liner 42 and/or the wrapsheet 66 or surge layer 60 need not be bonded to the absorbent structure 44. Alternatively, the liner 42 and/or the wrapsheet 66 or surge layer 60 can be adhesively bonded to the absorbent structure 44 and to each other in a windowpane design, whereby the active graphic 90 is free from contact with adhesive and the regions of the liner and/or the wrapsheet or surge layer surrounding the active graphic are in contact with a layer of adhesive. One suitable method and apparatus for adhesively bonding in a windowpane design is disclosed in U.S. Pat. No. 5,683,752 issued Nov. 4, 1997 to Popp et al., which is incorporated herein by reference to the extent it is consistent (i.e., not in conflict) herewith.

Figure 9:
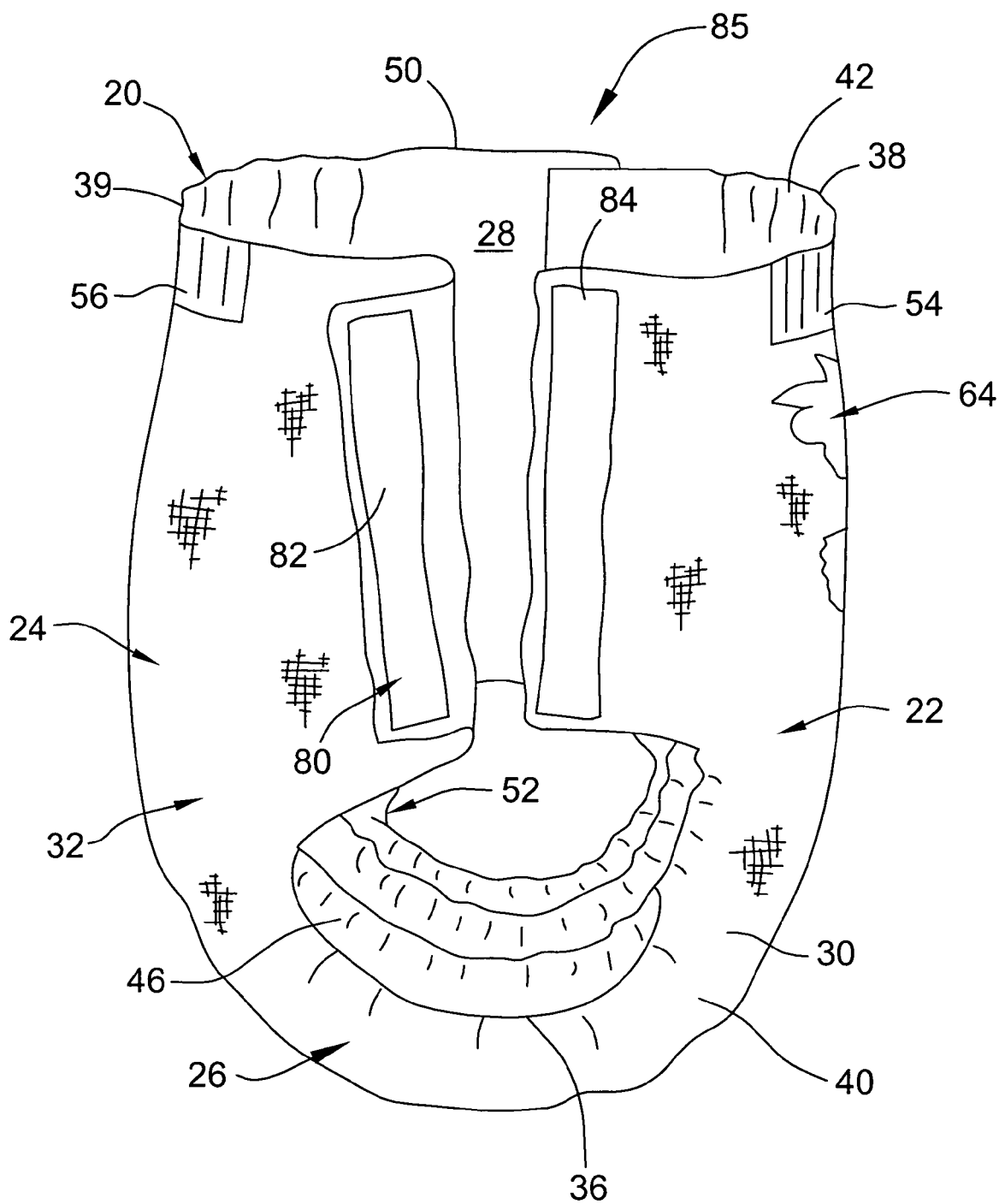
FIG. 9 illustrates a side perspective of another aspect of the present invention shown in the form of a pair of training pants having a pair of integral side panels and a mechanical fastening system fastened on one side of the training pants and unfastened on the opposite side thereof.
Figure 10:
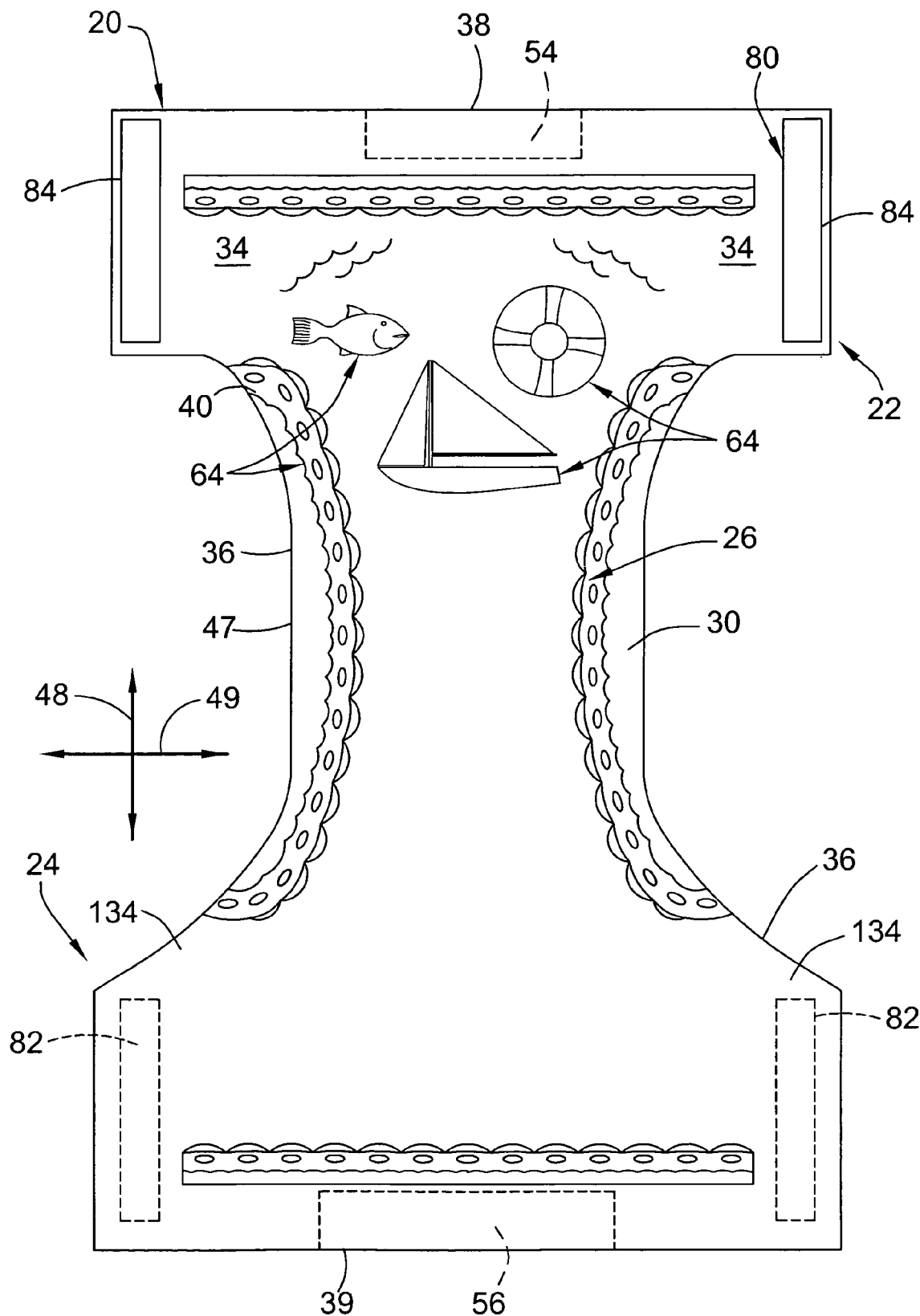
FIG. 10 illustrates a bottom plan view of the training pants of FIG. 9 with the pants in an unfastened, unfolded and laid flat condition, and showing the outer surface of the training pants that faces away from the wearer.
Figure 11:
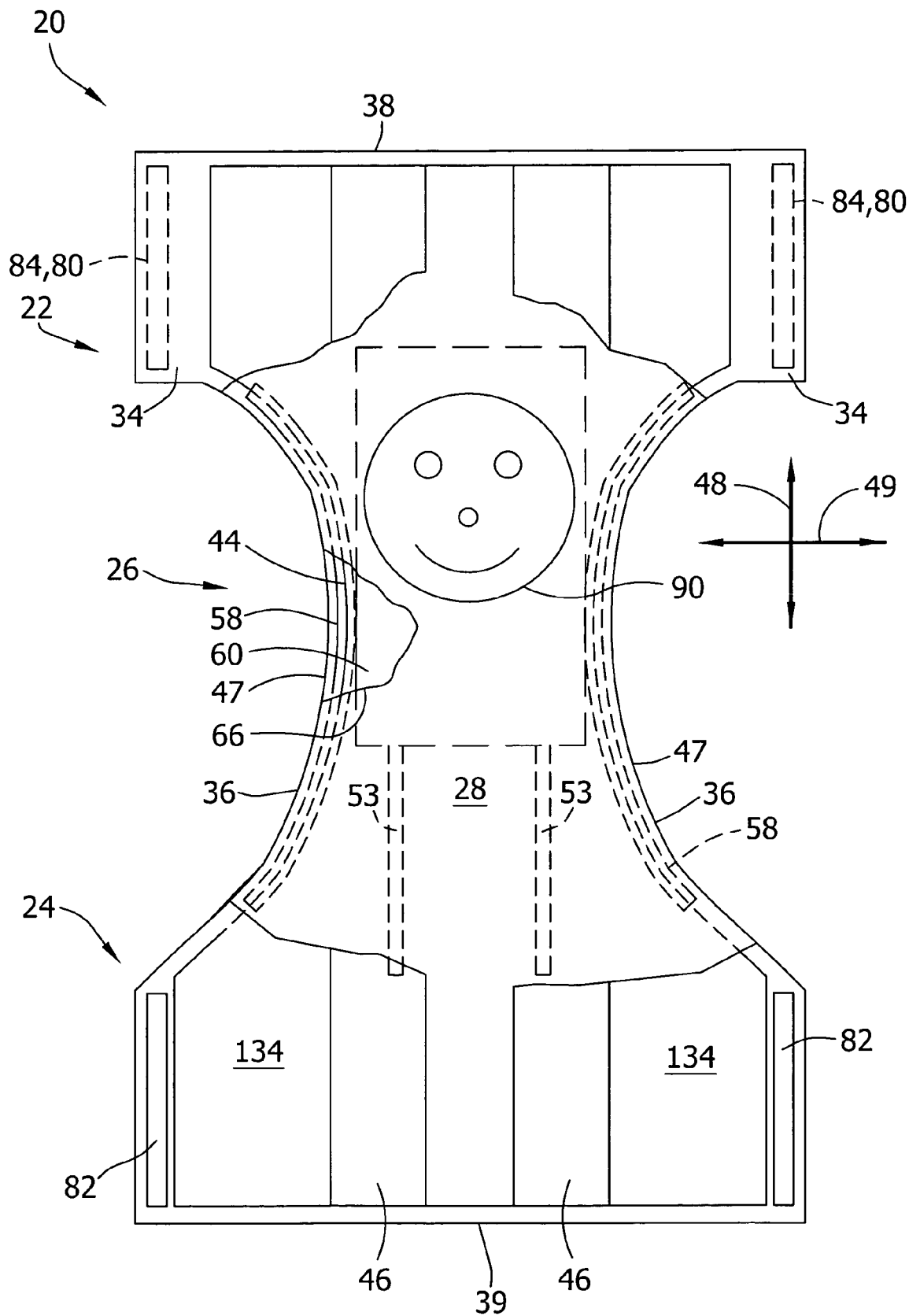
FIG. 11 illustrates a top plan view similar to FIG. 10 showing the inner surface of the training pants that faces the wearer when worn and with portions cut away to show underlying features.

FIGS. 9-11 illustrate another embodiment of the present invention wherein the absorbent article is the form of training pants 20 comprising a generally hourglass central absorbent assembly 32 and side panels 34, 134 integrally formed. The integrally formed side panels 34, 134 and absorbent assembly 32 comprise at least some common materials, such as the bodyside liner 42, flap composite, outer cover 40, or other materials to define a one-piece stretchable pants. As shown in FIG. 11, the absorbent structure 44 of this embodiment extends laterally outward at the front waist region 22 of the article 20 and the back waist region 24 of the article so that the absorbent structure is located between the bodyside liner 42 and the outer cover 40 at the side panels 34

The absorbent article 20 of the embodiments of FIGS. 9-11 has a graphic 90 that is visible from the inner surface 28 of the article. As in the previous embodiments, the graphic 90 may be an active graphic or a permanent graphic. Further, the graphic 90 may be located on the wrapsheet 66 enclosing the absorbent structure 44 and the surge layer 60. Also, the graphic 90 could be located on any other layer of the absorbent article 20 as discussed above for the previous embodiments.

Figure 12:
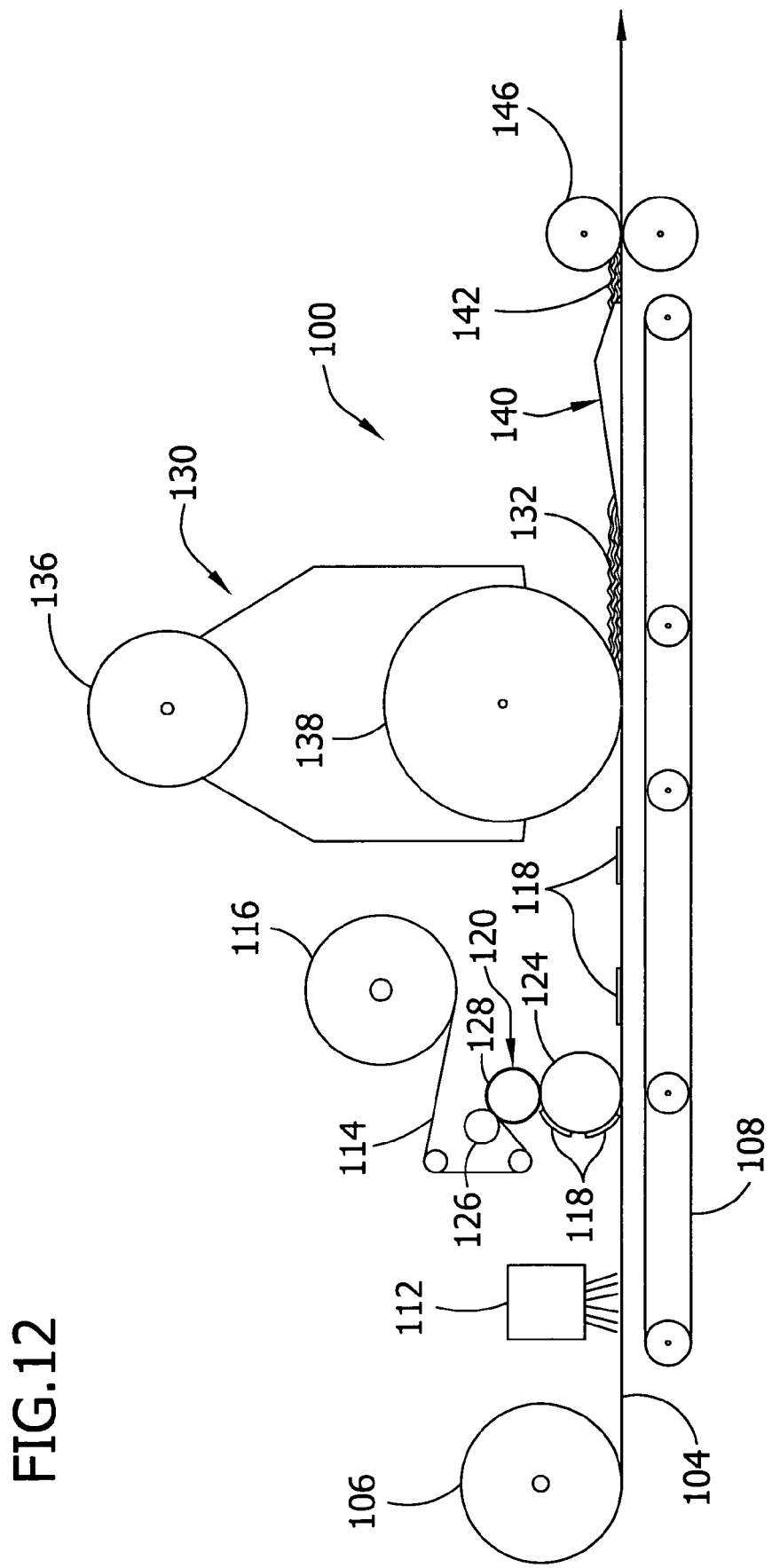
FIG. 12 is a schematic of an assembly section of manufacturing apparatus for manufacturing the absorbent article of the present invention having a graphic visible from the inner surface of the article.

One embodiment of an assembly section 100 for making a continuous stream of partially assembled garments is illustrated schematically in FIG. 12. The assembly section 100 can be used in combination with other equipment and processes adapted to manufacture training pants 20 shown in FIGS. 1-4. Reference may be made to U.S. Pat. Nos. 6,723,034 and 6,652,686 for additional steps in the process for manufacturing an absorbent article 20.

The various components of the training pant 20 can be connected together by any means known to those skilled in the art such as, for example, adhesive, thermal and/or ultrasonic bonds. Desirably, most of the components are connected using ultrasonic bonding for improved manufacturing efficiency and reduced raw material costs. Certain garment manufacturing equipment which is readily known and understood in the art, including frames and mounting structures, ultrasonic and adhesive bonding devices, transport conveyors, transfer rolls, guide rolls, tension rolls, and the like, have not been shown in FIG. 12. Suitable absorbent supply mechanisms, web unwinds, conveyor systems, registration systems, drives systems, control systems and the like, for use with the present process are disclosed in U.S. Pat. No. 5,766,389 issued Jun. 16, 1998 to Brandon et al., which is incorporated herein by reference.

A continuous supply of material 104 that forms the wrapsheet 66 is provided from a supply source 106. The supply source 106 can comprise for example any standard unwind mechanism, which generally includes a pair of spindles, a festoon assembly, and a dancer roll for providing wrapsheet material 104 at a desired speed and tension. The material 104 is continuously moved through the assembly section 100 by a conveyor 108 comprised of a porous belt moving over a vacuum box so that the material is drawn against the belt. It will be understood that the conveyor 108 may comprise any conventional web handling apparatus such as an impermeable conveyor belt, or the conveyor belt may be omitted and other conventional processes used such as drawing the wrapsheet material 104 through the machine without an underlying supporting structure along the length of the machine. The continuous supply of material 104 is supplied to any conventional apparatus for forming the absorbent article 20 such as the apparatus shown in the aforementioned incorporated references.

As shown in FIG. 12, a printer 112 is located generally adjacent the supply source 106 of wrapsheet material 104. As stated above, the printer 112 can comprise a conventional printing mechanism such as a flexographic printer as disclosed in U.S. Pat. No. 5,458,590 (Schleinz et al.); U.S. Pat. No. 5,566,616 (Schleinz et al.); U.S. Pat. No. 4,896,600 (Rogge et al.), and U.S. 2003/0019374A1 (Harte). Further, the printer 112 could be a sprayer for applying the graphic 90 to the material 104, an ink jet printer, or rotogravure printer.

A continuous web of material 114 used to form the surge layer 60 is provided from a suitable supply source 116. The supply source 116 can be any conventional mechanism for supplying surge material 114 such as a standard unwind mechanism. The surge layer material 114 may comprise either a continuous web or discrete sheets of material. In the illustrated embodiment, the surge material 114 is a continuous web that is cut into individual strips 118 and positioned on the wrapsheet 104 by an applicator device, generally indicated 120. One suitable applicator device 120 is disclosed in U.S. Pat. No. 5,104,116 issued Apr. 14, 1992 and U.S. Pat. No. 5,224,405 issued Jul. 6, 1993 both to Pohjola, which are incorporated herein by reference. The applicator device 120 can comprise a cutting assembly in the form of a rotatable knife roll 126 and a rotatable vacuum anvil roll 128 to cut individual strips 118 from the continuous surge layer material 114. The strips 118 cut by a blade on the knife roll 126 can be maintained on the anvil roll 128 by vacuum and transferred to a rotatable transfer roll 124.

The rotatable transfer roll 124 can comprise a plurality of vacuum pucks (not shown). The transfer roll 124 receives the strips 118 of material 114 from the anvil roll 128 and rotates to transfer the strips to the continuously moving wrapsheet material 104. When the strips 118 are positioned as desired relative to the wrapsheet material 104, the strips are released from the transfer roll 124 by extinguishing the vacuum in the pucks. The transfer roll 124 can continue to rotate toward the anvil roll 128 to receive other strips.

A supply source, generally indicated 130, for absorbent layer material 132 is provided to place absorbent material forming the absorbent structure 44 of the absorbent article 20 on the strips 118 of surge material 114 and the continuous supply of wrapsheet material 104. The supply source 130 can be any conventional mechanism for supplying the absorbent material 132. The absorbent material 132 can be supplied in a continuous layer of material or discrete structures. The supply source 130 comprises a hammermill 136 for forming fluff fibers and, if desired, for providing an enclosure for mixing superabsorbent material with the fluff fibers, and then depositing the fluff and superabsorbent material on a forming drum 138 having a desired absorbent design. The absorbent material 132 can be bonded to one or more other components using adhesives or other suitable means. Alternatively, composite absorbent materials or structures can be fed into the assembly process from rolls or compressed packages, such as festooned bales.

A wrapsheet folder assembly 140 receives the continuous web of wrapsheet material 104 that has passed through the printer 112, and received surge material 118 and absorbent material 132. The folder assembly 140 folds the wrapsheet 104 about the absorbent material 132 and surge material 118 to form an enclosed web of absorbent assembly material 142, commonly referred to as a "sausage", comprising absorbent structure material, surge material and wrapsheet material having at least one graphic printed thereon. The enclosed web of absorbent assembly material 142 is debulked by a debulker assembly 146 that receives the web. The debulker assembly 146 compresses the absorbent material 132 to increase the density and strength of the material and decrease the thickness of the absorbent assembly material 142. It is understood, though, that the debulker assembly may be omitted from the assembly section 100 without departing from the scope of this invention. The absorbent assembly material 142 is conveyed to the conventional portion of the assembly apparatus (not shown) where the web of material is cut into discrete absorbent assemblies that form the central absorbent assemblies 32 of the training pants 20.

The process of assembling the absorbent assemblies with assembly section 100 efficiently assembles the absorbent assemblies used in the training pants by placing the surge layer material 118 on the continuous wrapsheet material 104 prior to the application of absorbent structure material 132 to the wrapsheet. By applying the surge layer 118 before the absorbent structure 132, the surge layer is placed on the wrapsheet material 104 having the graphic printed thereon and may be enclosed by the folding station that is used to fold the wrapsheet layer and enclose the absorbent assembly. The surge supply source 116 may be incorporated into the process for manufacturing the article 20 by placing the surge supply source in existing open space in the manufacturing assembly upstream of the absorbent layer supply source 130, so that the existing components of the apparatus do not have to be repositioned to accommodate the addition of the surge layer material 118 to the process.

Figure 13:
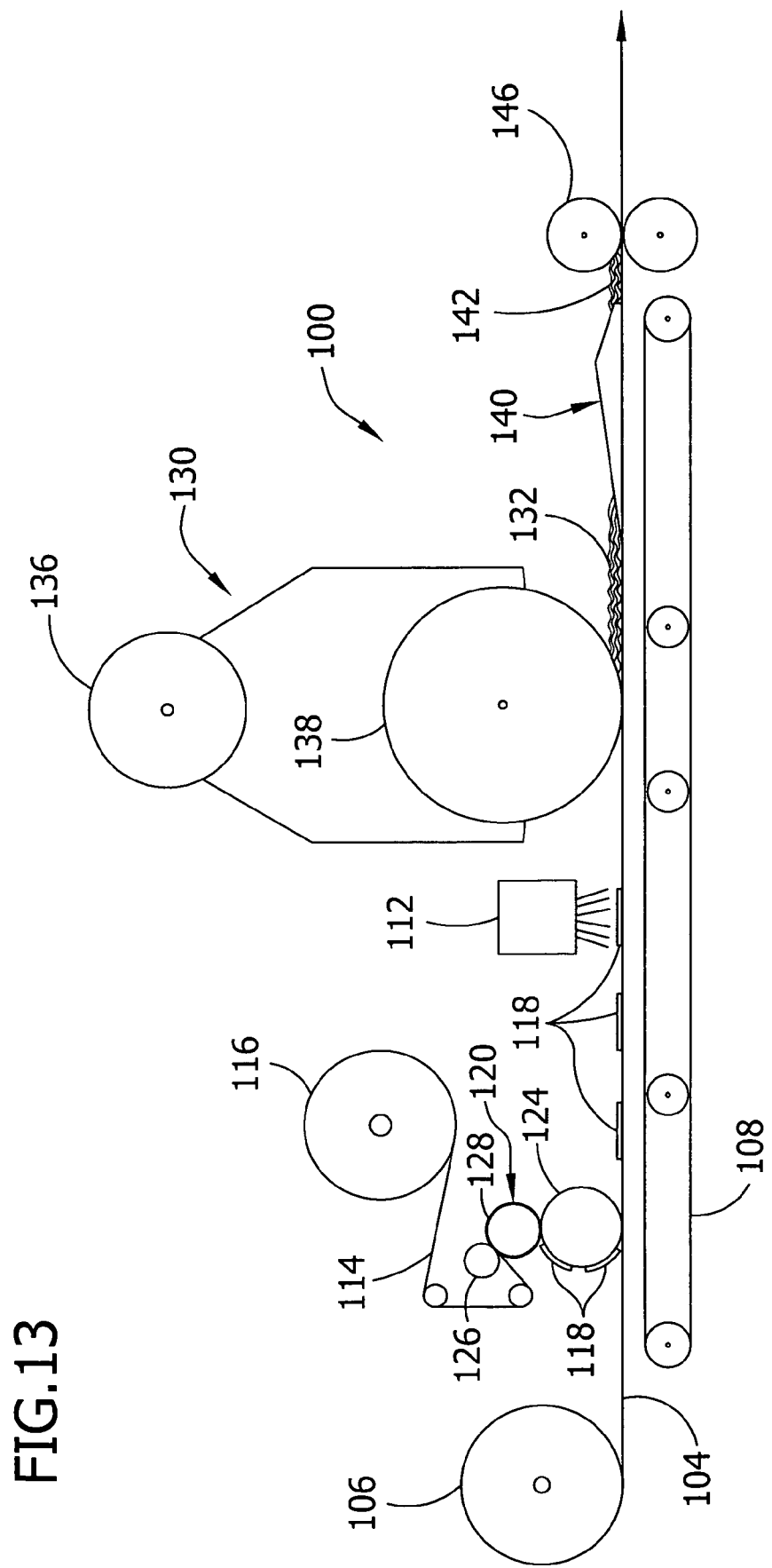
FIG. 13 is a view similar to FIG. 12 but showing an alternative embodiment of an assembly section of manufacturing apparatus for manufacturing an absorbent article.
Figure 14:
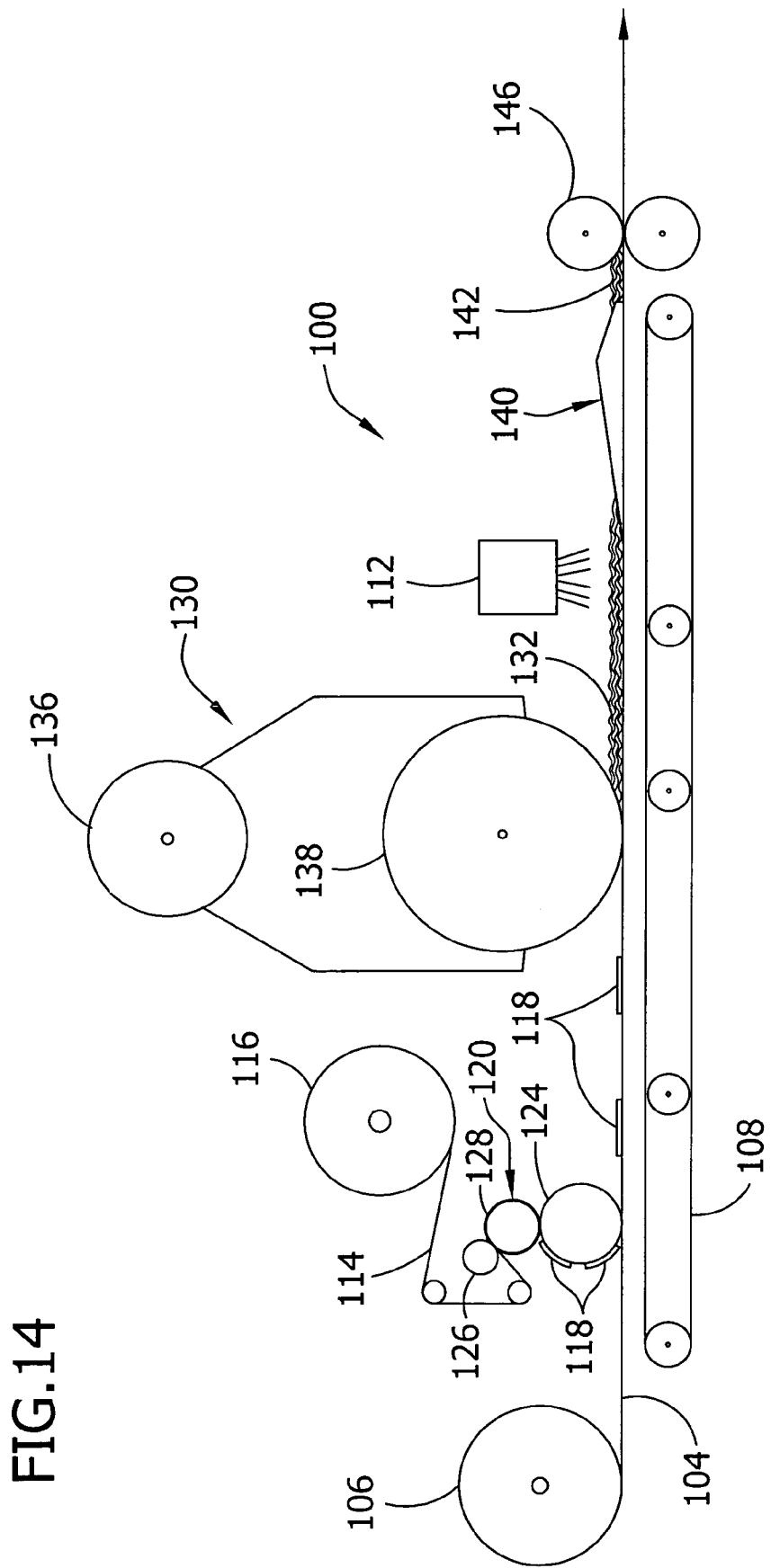
FIG. 14 is a view similar to FIG. 12 but showing an alternative embodiment of an assembly section of manufacturing apparatus for manufacturing an absorbent article.

It will be understood that the assembly section 100 may be modified such that surge layer 118 and/or wrapsheet material 104 are omitted from the manufacturing process for the absorbent article 20. Further, the printer 112 may be positioned at any point in the assembly section 100 so that the graphic 90 is printed on materials other than the wrapsheet material 104. For example, as shown in FIG. 13, the printer 112 could be positioned between the surge supply source 116 and the absorbent layer supply source 130 so that the graphic is printed on the surge layer 118. Alternatively, as shown in FIG. 14, the printer 112 could be positioned downstream of the absorbent layer supply source 130 so that the graphic is printed on the absorbent structure material 132 prior to the folding of the wrapsheet material 104 by the folding apparatus 140. Also, the printer 112 may be located such that the printer places the graphic on either side of the surge layer 118 or either side of the absorbent structure material 132.

It will be understood that the printer 112 could be eliminated from the process of manufacturing the article 20 by including a graphic 90 that is pre-printed onto the wrapsheet material 104 that is supplied from the supply source 106. Further, the graphic 90 could be printed on the web of surge layer material 114 supplied from the supply source 116. Also, it is contemplated that one or more article components (e.g., surge layer 118 and/or absorbent structure material 132) may be conveyed in a direction 90 degrees to the line of motion of the wrapsheet material 104, or other moving web of material, and cut and placed on the wrapsheet material. The printer 112 may be positioned to print graphics on components oriented 90 degrees from the line of motion of the wrapsheet material 104 or such components may be pre-printed with graphics and assembled on the moving web of material.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An absorbent article having an inner surface adapted to be disposed toward a wearer of the article and an outer surface opposite said inner surface, said article comprising:
    an outer cover at least in part defining the outer surface of the article;
    a liner in opposed relationship with the outer cover and at least in part defining the inner surface of the article;
    an absorbent structure disposed between the liner and the outer cover;
    at least one graphic disposed intermediate the liner and the outer surface of the article and being free from direct contact with the liner, said article being configured such that the graphic is visible from the inner surface of the article.

2. The absorbent article set forth in claim 1 wherein said at least one graphic is an active graphic.

3. The absorbent article set forth in claim 2 wherein said active graphic is a fading graphic.

4. The absorbent article of claim 2 wherein said active graphic is an appearing graphic.

5. The absorbent article of claim 1 wherein said absorbent structure has a liner-facing surface and a cover-facing surface and said at least one graphic is disposed between the liner-facing surface of the absorbent structure and said inner surface of the article.

6. The absorbent article of claim 1 further comprising a wrapsheet surrounding at least a portion of said absorbent structure such that at least a portion of the wrapsheet is disposed between the absorbent structure and the liner.

7. The absorbent article set forth in claim 6 further comprising a surge layer disposed between a liner-facing surface of the absorbent structure and said portion of the wrapsheet, said surge layer having a liner-facing surface and a cover-facing surface.

8. The absorbent article set forth in claim 7 wherein said graphic is disposed on the portion of the wrapsheet between the liner-facing surface of the surge layer and the liner.

9. The absorbent article set forth in claim 7 wherein said graphic is disposed on the liner-facing surface of the surge layer.

10. The absorbent article set forth in claim 7 wherein said graphic is disposed on the cover-facing surface of the surge layer.

11. The absorbent article set forth in claim 1 wherein said graphic is disposed on the absorbent structure.

12. The absorbent article set forth in claim 11 wherein said graphic is disposed on a liner-facing surface of the absorbent structure.

13. An absorbent article having an inner surface adapted to be disposed toward a wearer of the article and an outer surface opposite said inner surface, said article comprising:
    an outer cover at least in part defining the outer surface of the article;
    a liner in opposed relationship with the outer cover and at least in part defining the inner surface of the article;
    an absorbent structure disposed between the liner and the outer cover;
    at least one fading graphic comprising an ink soluble in urine, the fading graphic being disposed intermediate the inner surface and the outer surface of the article and free from direct contact with the liner, said article being configured such that the graphic is visible from the inner surface of the article while inhibiting ink from the graphic from bleeding onto the wearer of the article.

14. The absorbent article of claim 13 wherein said absorbent structure has a liner-facing surface and a cover-facing surface and said at least one fading graphic is disposed between the liner-facing surface of the absorbent structure and said inner surface of the article.

15. The absorbent article of claim 13 further comprising a wrapsheet surrounding at least a portion of said absorbent structure such that at least a portion of the wrapsheet is disposed between the absorbent structure and the liner.

16. The absorbent article of claim 15 wherein said at least one fading graphic is disposed on said portion of the wrapsheet disposed between the absorbent structure and liner.

17. The absorbent article set forth in claim 15 further comprising a surge layer disposed between a liner-facing surface of the absorbent structure and said portion of the wrapsheet, said surge layer having a liner-facing surface and a cover-facing surface.

18. The absorbent article set forth in claim 13 wherein said at least one fading graphic is disposed on the absorbent structure.

19. The absorbent article set forth in claim 18 wherein said at least one fading graphic is disposed on a liner-facing surface of the absorbent structure.

* * * * *